United States Patent
El-Sawy et al.

(10) Patent No.: US 10,653,739 B2
(45) Date of Patent: May 19, 2020

(54) MEDICINAL AMBROSIA MARITIMA EXTRACTS

(71) Applicants: Mohamed Fakhr EL-Din El-Sawy, Alexandria (EG); Layla Mohamed Fakhr El-Din El-Sawy, Alexandria (EG); Sherine Hassan Abbas Helmy, Alexandria (EG); Mark Lawrence Day, Gregory, MI (US); John Ronald Rubin, Ann Arbor, MI (US); Guadalupe Lorenzatti, Ypsilanti, MI (US)

(72) Inventors: Mohamed Fakhr EL-Din El-Sawy, Alexandria (EG); Layla Mohamed Fakhr El-Din El-Sawy, Alexandria (EG); Sherine Hassan Abbas Helmy, Alexandria (EG); Mark Lawrence Day, Gregory, MI (US); John Ronald Rubin, Ann Arbor, MI (US); Guadalupe Lorenzatti, Ypsilanti, MI (US)

( * ) Notice: Subject to any disclaimer, the term of this patent is extended or adjusted under 35 U.S.C. 154(b) by 398 days.

(21) Appl. No.: 15/261,650

(22) Filed: Sep. 9, 2016

(65) Prior Publication Data
US 2017/0071994 A1    Mar. 16, 2017

Related U.S. Application Data

(60) Provisional application No. 62/344,124, filed on Jun. 1, 2016, provisional application No. 62/217,609, filed on Sep. 11, 2015.

(51) Int. Cl.
*A61K 36/28* (2006.01)
*A61K 31/365* (2006.01)

(52) U.S. Cl.
CPC ............ *A61K 36/28* (2013.01); *A61K 31/365* (2013.01); *A61K 2236/35* (2013.01); *A61K 2236/53* (2013.01); *A61K 2236/55* (2013.01)

(58) Field of Classification Search
None
See application file for complete search history.

(56) References Cited

U.S. PATENT DOCUMENTS

2007/0098827 A1    5/2007    Ripoll

FOREIGN PATENT DOCUMENTS

CN    104086558    10/2014

OTHER PUBLICATIONS

Hejchman, et al., J. Med. Chem., 38:3407. (Year: 1995).*
Herz, et al., Phytochemistry, 20:1601. (Year: 1981).*
Payne, W., Plant Syst. Evol., 125:169. (Year: 1976).*
Jakupovic, et al., Planta Medica, 53:49. (Year: 1987).*
Abu-Shady, et al., J. Am. Pharm. Assoc., 42:387. (Year: 1953).*
Partial Search Report for related case, App. No. PCT/US16/51121, dated Nov. 10, 2016.
Herz et al., "Damsinic Acid and Ambrosanolides from Vegetative Ambrosia Hispida", Phytochem. 20:7, pp. 1601-1604 (1981).
Ibrahim et al., "A Phytopharmacological Review on Four Antitumor Medicinal Plants Grown in Sudan", Am. J. PharmTech Res., 4:5, p. 27-41 (2014).
Search Report for related case, App. No. PCT/US16/51121, dated Feb. 16, 2017.
Villagomes et al. "Multiple Anticancer Effects of Damsin and Coronopilin Isolated from Ambrosia arborescens on Cell Cultures" Anticancer Res. Sep. 2013; 33(9)3799-805. Abstract; p. 3803, col. 2, para 2.
EP Search Report for related case, App. No. EP16845196, dated Feb. 11, 2019.
Makkawi Ali JJ, et al. "Phytochemical and biological evaluation of Ambrosia maritima." Research Journal of Pharmaceutical Biological and Chemical Sciences 6.4 (2015): 1678-1688.
Kreuger Maria Regina Orofino, et al. "Sesquiterpene lactones as drugs with multiple targets in cancer treatment: focus on parthenolide." Anti-cancer drugs 23.9 (2012): 883-896.
Nagaya H., et al. "Cytotoxic chemical constituents from Egyptian medicinal plant, *Ambrosia maritima* L." Natural Medicines (Tokyo) 48 (1994): 223-226.

* cited by examiner

*Primary Examiner* — Michael Barker
(74) *Attorney, Agent, or Firm* — Boulware & Valoir

(57) ABSTRACT

Phytoceutical compositions from organic extracts of the *Ambrosia maritima* or *Ambrosia hispida* plants and uses thereof for treatment of cancers is described.

7 Claims, 33 Drawing Sheets

MEDICINAL AMBROSIA MARITIMA EXTRACTS

PRIOR RELATED APPLICATIONS

This invention claims priority to U.S. 62/344,124, filed on Jun. 1, 2016, and U.S. 62/217,609, filed on Sep. 11, 2015. Both of which are incorporated by reference in their entirety herein.

FEDERALLY SPONSORED RESEARCH STATEMENT

Not applicable.

REFERENCE TO MICROFICHE APPENDIX

Not applicable.

FIELD OF THE DISCLOSURE

The disclosure relates to the field of cancer therapy, and in particular to the field of phytoceutical compositions for the treatment of cancer.

BACKGROUND OF THE DISCLOSURE

Plant based therapeutics have been known and used since ancient times, and still provide between 30-40% of our new drug candidates each year. The complexity of the components contained within plants are not fully understood and it is appreciated that an in-depth biochemical analysis of the components of plants as they are found e.g. in leaves, stems, and the like, may continue to reveal valuable therapeutic compounds for the treatment of various illnesses as diverse as microbial infections or migraines.

Recently, there has been considerable interest in searching the phytochemical properties of many long ago discovered plants to determine their potential pharmaceutical benefits, most particularly, on secondary metabolites. In addition to the primary metabolism necessary for life, plants have a secondary metabolism that generates compounds, which aid in their growth and development. A common role of secondary metabolites is defense mechanisms to fight off animals, pest and pathogens. These compounds have become the focus of much pharmacological interest.

One such family of interest for natural therapeutics is the family Asteraceae (or Compositae). This family has a remarkable ecological and economical importance and is present from the polar regions to the tropics, colonizing all available habitats, though it is most commonly found in arid areas. Asteraceae has been regarded as a promising family of plants because of the amount and variety of active compounds produced by the secondary metabolism. Some commonly known uses of the Asteraceae family is in herbal products such as teas (Chamomile, *Echinacea*) or potpourri (Marigold). However, there is evidence that Asteranceae contains secondary metabolites that can be beneficial in the treatment of many diseases.

Cancer is a general term frequently used to indicate any of the various types of malignant neoplasms (i.e. abnormal tissue that grows by cellular proliferation more rapidly than normal), most of which invade surrounding tissue, may metastasize to several sites, are likely to recur after attempted removal, and cause death unless adequately treated. Although a variety of approaches to cancer therapy, including surgical resection, radiotherapy, and chemotherapy, have been available and commonly used for many years, cancer remains one of the leading causes of death in the world.

Cancer implicates several important signal pathways in the affected cells. The balance between proliferation and programmed cell death is disturbed in a patient having cancer, and certain genetic disturbances of apoptotic signaling pathways have been found in carcinomas, leading to tumor development and progression. Much work in cancer research targets the signal pathways as means of stopping cancer progression and treating the patient.

Many compounds naturally occurring in plants have been shown to elicit some improvements to cancer treatment, side effects of cancer treatments, and/or the progression of cancer itself. However, there exists a need to find and develop more plant-based compounds for cancer treatment and to understand how they affect the signal pathways so that the compounds can be combined for a more effective treatment plan.

SUMMARY OF THE DISCLOSURE

Disclosed herein are several pharmaceutical compounds extracted from a member of the plant family Asteraceae and methods of using these compounds for cancer treatment. These compounds have been proven efficacious against bladder, prostate, triple negative breast cancer (TNBC), regular and chemo-resistant lung cancer, and pancreatic cancer in laboratory models in vitro and in vivo animal models. Further, the compounds have been shown to inhibit primary and secondary sphere formation, which could lead to treatment and elimination of circulating tumor cells.

The present compounds relate to an extract of pharmaceutical potential derived from the organic fraction of Asteracea plants, including *Ambrosia maritima* or *Ambrosia hispida*. *Ambrosia maritima* is richly branched and has grey-hairy aromatic fragrant leaves and green, solid and striated stems with faint ridges. This plant can be found mainly in the coastal strip of North Africa's Mediterranean region and along the muddy canal banks of the Nile in Egypt and Sudan. *Ambrosia hispida*, also known as Coastal Ragweed, is native to North American, mainly north of Mexico. It, too, is a woody plant with a silver/gray broad leaf.

Many studies on *Ambrosia maritima* have shown that it has some pharmacological action. A study conducted by Alard et al. showed no toxic signs could be detected after oral administration of 5 g/kg of dried leaves of the plant as a powder nor as a methanolic extract, nor after the incorporation of 50,000 ppm powdered leaves in the feed for a duration of 4 weeks. Further, no mutagenic effect could be detected in mutagenicity test using *Salmonella typhimurium* strains TA97, TA 98, TA1538, TA100 and TA1535 (Alard 1991).

*Ambrosia maritima* has been shown to kill the intermediate host of *Schistosomiasis* and *Fascioliasis* (both parasitic infections) at a concentration of 3000 mg/L in water streams (M. F. El-Sawy 1977 and 1986). Some compounds within *Ambrosia maritima* have considerable cytotoxic effect (Abdallah 1991) and antimicrobial activity (Badawy 2014). Further, *Ambrosia maritima* has shown use as a muscle relaxant of the intestine, uterus and blood vessels; to increase urine output/day; and, to help to decrease body weight.

*Ambrosia maritima* and *Ambrosia hispida* contain several compounds with possible pharmacological effects, such as chloroambrosin, ambrosin, damsin, neoambrosin, farnserin, hymendin, hymenin, stamonin-b, anhydrofranserin, triterpenes, s-amyrin, apigenin, coumarins, sterols, β-sitosterol, tannin, volatile oil, carvone, comphor, caryophyllene, cineole, salts and other sesquiterpene lactones. However, the present methods focus on the use of sesquiterpene lactones.

Sesquiterpene lactones (SL) are compounds found in the organic fraction of the plant extract. The SLs in this organic extract are mostly bifunctional sesquiterpene lactones and we have found that they react specifically and covalently with cysteine side chains of target proteins in cancer cells. The α,β-unsaturated ketone moieties of the plant derived sesquiterpene lactones behave as Michael acceptors in spontaneous reactions with protein cysteine sulfhydryl Michael donors under physiological conditions. FIG. 1A displays a typical bifunctional sesquiterpene lactone with arrows pointing at the two Michael acceptor sites, which allows the SL to act as a crosslinker between two protein cysteine side chains. However, several of the SLs found in *Ambrosia maritima* contain two or more Michael acceptor sites in the same molecule. FIG. 1B displays three other SLs found in extracts from *Ambrosia* plants.

SLs are also pleiotropic compounds that exhibit and target more than one signaling molecule within a cell and show the ability to directly bind to diverse proteins with high affinity. Thus, the therapeutic effects of forming covalent adducts on multiple target proteins include blocking cancer cell proliferation pathways (i.e. NF-κB and STAT3) and promoting apoptotic cell-killing pathways (i.e. Caspases 3, 7, and 6).

Many different SLs are present in the *Ambrosia maritima* and *Ambrosia hispida* organic extract, including ambrosin, damsin, neoambrosin, parthenin, helenalin, tribromoambrosin and the like. The present methods preferable uses the entire spectrum of SLs found in the organic extract for treatment. However, it is possible to separate out and purify individual SLs for treatment or to synthesize specific SLs by organic chemistry methods. While it is expected that most cancer cells will respond to the entire spectrum of SLs found in an organic extract from an *Ambrosia* plant, some cancers may also benefit from treatment with the individual SLs or a subset of SLs found in the organic extract. The selection of individual SLs from the whole extract can be tunable, thus allowing the purified individual SLs to be combined in ratios not normally found in the organic extract.

In the present methods, the *Ambrosia maritima* or *Ambrosia hispida* plant is mixed with an organic solvent such as acetonitrile, methanol, ethanol, isopropanol, ether, ethyl acetate, acetone or mixtures thereof to extract the SLs. A polar organic solvent is preferably used.

Generally the mixture of plant tissue and polar organic solvent will be left to stand, thereby allowing the extraction to take place. Alternatively, the plant tissue may be exhaustively extracted with a polar organic solvent in a Soxhlet apparatus or the like.

The plant tissue may be fresh, frozen or dried and may be in comminuted form. The extract is then generally separated from the plant tissue and the solvent removed from the solvent extract by drying or precipitation and the like. Following removal of the solvent, the remaining primary extract may be further purified by known techniques such as size exclusion chromatography, ion exchange chromatography, HPLC, precipitation, crystallization, further solvent extraction, and reverse phase chromatography, and the like. The remaining plant tissue may be further extracted using the same or an alternative solvent.

FIG. 1C-D displays the chromatographic fingerprints of the SLs in the organic extracts of *Ambrosia maritima* (1C) and *Ambrosia hispida* (1D). Both resulted in a similar composition of sesquiterpene lactone, which indicates that there are many plants in the Asteraceae family that can be use for the pharmaceutical preparation described herein.

The active ingredient or ingredients of the organic extract of plant material can be used as is, or can be formulated with known pharmaceutically acceptable carriers, diluents and/or excipients.

For example, gelatin capsules containing dried organic and/or purified compounds of the extract can be produced containing a suitable dose of the active ingredient(s). Optionally, packets containing the dried extract can be provided for mixture with e.g., hot fluids, to be taken orally. The extract can also be formulated with solid carriers for pressing into pill or tablet forms, especially with delayed release excipients for formulating once a day pill/tablet forms. Other pharmaceutical formulations could be liquid or solid carriers and/or excipients to be administered orally.

The pharmaceutically acceptable carrier could also be a nanobiological carrier such as a High Density Lipoprotein that will specifically home in and target the tumor in a patient with cancer. Antibodies can also be used for such targeting.

It may also be possible to prepare forms of the active ingredients suitable for non-oral routes of administration, such as inhalational, buccal, sublingual, nasal, suppository or parenteral dosage forms.

In more detail, the invention may comprise one or more of the following:

A composition comprising an organic extract of *Ambrosia maritima* together with a pharmaceutically acceptable carrier; an organic extract of *Ambrosia maritima* that is 10, 100 or 1000 fold or more stable than a natural cellular form of the SLs when assayed against a raw cellular extract of plant material; an organic extract of *Ambrosia maritima* that is at least 100 fold more concentrated than a natural cellular form of the SLs, preferably 1000 fold, or 10,000 fold or better; any of the compositions described herein further comprising a pharmaceutical acceptable excipient, buffer, chelator, or delayed release matrix or combinations thereof; any of the composition herein described in gelatin capsule form, pill form, or liquid form for oral use.

A composition comprising an organic extract of *Ambrosia hispida* together with a pharmaceutically acceptable carrier; an organic extract of *Ambrosia hispida* that is 10, 100 or 1000 fold or more stable than a natural cellular form of the SLs when assayed against a raw cellular extract of plant material; an organic extract of *Ambrosia hispida* that is at least 100 fold more concentrated than a natural cellular form of the SLs, preferably 1000 fold, or 10,000 fold or better; any of the compositions described herein further comprising a pharmaceutical acceptable excipient, buffer, chelator, or delayed release matrix or combinations thereof; any of the composition herein described in gelatin capsule form, pill form, or liquid form for oral use.

A method of treating cancer, comprising administering an effective amount of any of the above compositions to a patient with cancer; a method of treating triple negative breast cancer (TNBC), comprising administering an effective amount of the composition described to a patient with TNBC; a method of treating bladder cancer, comprising administering an effective amount of the composition described to a patient with bladder cancer; a method of treating lung cancer, comprising administering an effective amount of the composition described to a patient with lung cancer; a method of treating prostate cancer, comprising administering an effective amount of the composition described to a patient with prostate cancer.

A method of preparing the pharmaceutical composition described, said method comprising comminuting *Ambrosia maritima*, extracting an organic soluble component from said comminuted *Ambrosia maritima* and adding a pharmaceutically acceptable carrier to said organic soluble component; a method of preparing the pharmaceutical composition herein, said method comprising comminuting *Ambrosia maritima*, extracting an organic soluble component(s) from said comminuted whole plant, purifying the extracted organic soluble compound(s), and adding a pharmaceutically acceptable carrier to said purified organic soluble component(s).

A method of preparing the pharmaceutical composition described, said method comprising comminuting *Ambrosia hispida*, extracting an organic soluble component from said comminuted *Ambrosia hispida* and adding a pharmaceutically acceptable carrier to said organic soluble component; a method of preparing the pharmaceutical composition herein, said method comprising comminuting *Ambrosia hispida*, extracting an organic soluble component(s) from said comminuted whole plant, purifying the extracted organic soluble compound(s), and adding a pharmaceutically acceptable carrier to said purified organic soluble component(s).

The pharmaceutical composition can be administered daily, 3-4 times a week or weekly. The length of dosing is at least 6 weeks, wherein preferred dosing ranges are 6-12 weeks, 8-10 weeks or 9 weeks. Daily treatment by oral administration for 6-12 weeks is preferred, but in some cases, the length of time would be extended according to the extent of the cancer and its grade.

This summary is provided to introduce a selection of concepts that are further described below in the detailed description. This summary is not intended to identify key or essential features of the claimed subject matter, nor is it intended to be used as an aid in limiting the scope of the claimed subject matter.

As used herein, "plant matter" refers to any part or parts of the plant taken either individually or in a group and is not limited to leaves, flowers, roots and stems.

The term "organic extract," as used herein, refers to a composition prepared by contacting plant material with an organic solvent following procedures such as those described herein. The term encompasses crude extracts, prepared by a simple organic extraction, as well as crude extracts that have been subjected to one or more separation and/or purification steps, including substantially purified and purified active ingredient(s) and concentrates or fractions derived from a crude extract by subjecting the crude extract to one or more additional extraction, concentration, fractionation, filtration, condensation, distillation or other purification step. The plant extract may be in liquid form, such as a solution, concentrate or distillate, semiliquid form, such as a gel or paste, or it may be in solid form, such as in granulate or powder form. The plant matter may be fresh, dried, frozen, or in a comminuted form.

The term "active ingredient" includes one or more active ingredients (e.g., compounds having pharmaceutically efficacy against at least bladder, prostate, and breast cancer, and possibly other diseases) isolatable from at least the *Ambrosia maritima* and/or *Ambrosia hispida*, and potentially from other *Ambrosia* species or even other plant families. It includes both synthetic (chemically made) and natural (derived from plants) forms of the active ingredient.

The term "isolated," when used in reference to a compound or compounds having pharmaceutical activity, refers to a form of the active ingredient that is relatively free of proteins, nucleic acids, lipids, cell wall, carbohydrates or other materials with which it is naturally associated in a live plant.

The term "concentrated" when used in reference to an active ingredient, refers to a form of the active ingredient that is at least 50% pure when analyzed by HPLC.

The term "substantially purified," when used in reference to an active ingredient, refers to a form of the active ingredient that is at least 75% pure when analyzed by HPLC.

The term "purified," when used in reference to an active ingredient refers to a form of the compound(s) that is at least 90% pure, and preferably is at least 95, 98 or 99% pure when analyzed by HPLC.

The terms "therapy," and "treatment," as used interchangeably herein, refer to an intervention performed with the intention of improving a recipient's medical status. The improvement can be subjective or objective and is related to the amelioration of the symptoms associated with, preventing the development of, or altering the pathology of a disease, disorder or condition being treated. Thus, the terms therapy and treatment are used in the broadest sense, and include the prevention (prophylaxis), moderation, reduction, and curing of a disease, disorder or condition at various stages. Prevention of deterioration of a recipient's status (i.e. stabilization of the disease, disorder or condition) is also encompassed by the terms. Those in need of therapy/treatment include those already having the disease, disorder or condition as well as those prone to, or at risk of developing, the disease, disorder or condition and those in whom the disease, disorder or condition is to be prevented.

The term "subject" or "patient," as used herein, refers to an animal in need of treatment. The term "animal," as used herein, refers to both human and non-human animals, including, but not limited to, mammals, birds and fish.

As used herein, "effective amount" refers to the amount of organic extract or SL required to confer a biological or meaningful patient benefit, such as the biological or medical response or improvement sought by a medical doctor or other medical professional. In one aspect, the term "effective amount" is intended to mean the amount of drug that will bring about a biologically meaningful improvement in the subject's cancer growth, symptom, or disease. Doses that exhibit large therapeutic indices are preferred. Effective amounts may vary, as recognized by those skilled in the art, depending, for example, on route of administration, dosage form, inclusion of additional active agents, as well as age, weight, sensitivity, type of cancer and health of the subject.

The term "phytoceutical," as used herein, refers to a plant-comprising composition having therapeutic properties.

As used herein, "protease 'nicks'" means processing, maturation and activating other proteins (e.g. Caspases).

A "significant percentage of change" for imaging results was considered to be 10% and above on the quantifying pixel density for each spot in the Image Microarray Profile. Calculating any difference between the control and treatment wherein any difference above 10% was considered significant.

The use of the word "a" or "an" when used in conjunction with the term "comprising" in the claims or the specification means one or more than one, unless the context dictates otherwise.

The term "about" means the stated value plus or minus the margin of error of measurement or plus or minus 10% if no method of measurement is indicated.

The use of the term "or" in the claims is used to mean "and/or" unless explicitly indicated to refer to alternatives only or if the alternatives are mutually exclusive.

The terms "comprise", "have", "include" and "contain" (and their variants) are open-ended linking verbs and allow the addition of other elements when used in a claim.

The phrase "consisting of" is closed, and excludes all additional elements.

The phrase "consisting essentially of" excludes additional material elements, but allows the inclusions of non-material elements that do not substantially change the nature of the invention.

The following abbreviations are used herein:

| ABBREVIATION | TERM |
| --- | --- |
| Cys | Cysteine |
| EGFR | epidermal growth factor receptor |
| ER-α | Estrogen Receptor Alpha |
| GPR30 | G-Protein Coupled Receptor 30 |
| HPLC | High-Performance Liquid Chromatography |
| $IC_{50}$ | Half Maximal Inhibitory Concentration |
| MTS | [3-(4,5-dimethylthiazol-2-yl)-5-(3-carboxymethoxyphenyl)-2-(4-sulfophenyl)-2H-tetrazolium salt, or Owen's reagent |
| NOD/SCID | Non-obese Diabetic/Severe Combined Immunodeficient |
| SL | Sesquiterpene lactones |
| TNBC | triple negative breast cancer |
| kDa | kilo-daltons |

DESCRIPTION OF EMBODIMENTS OF THE DISCLOSURE

Figure 1A:
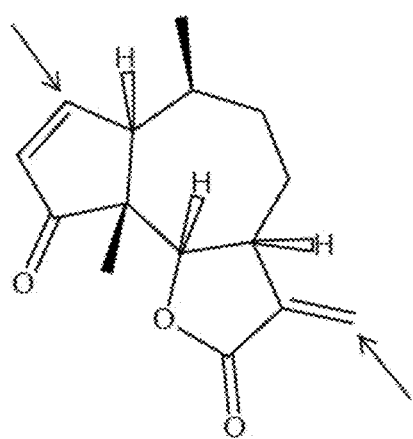
FIG. 1A. Chemical structure of exemplary SL Ambrosin with arrows pointing to the Michael reaction points.
Figure 1B:
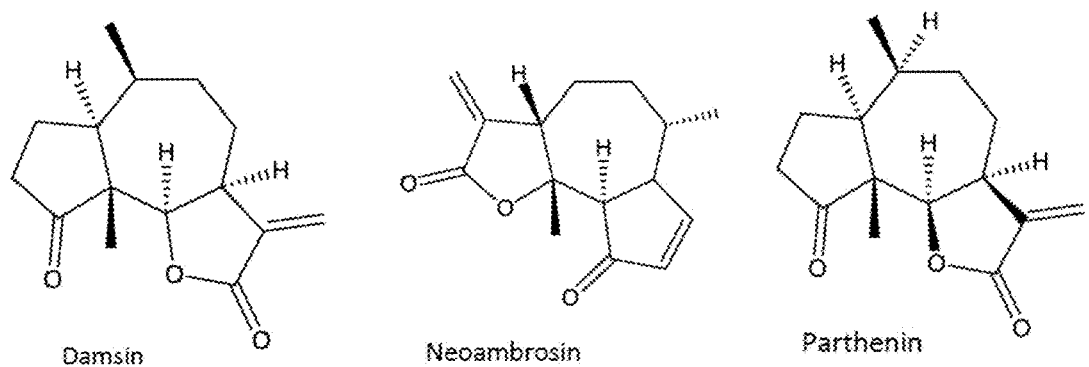
FIG. 1B. Chemical structure of three additional exemplary SLs found in *Ambrosia* plants.
Figure 1C:
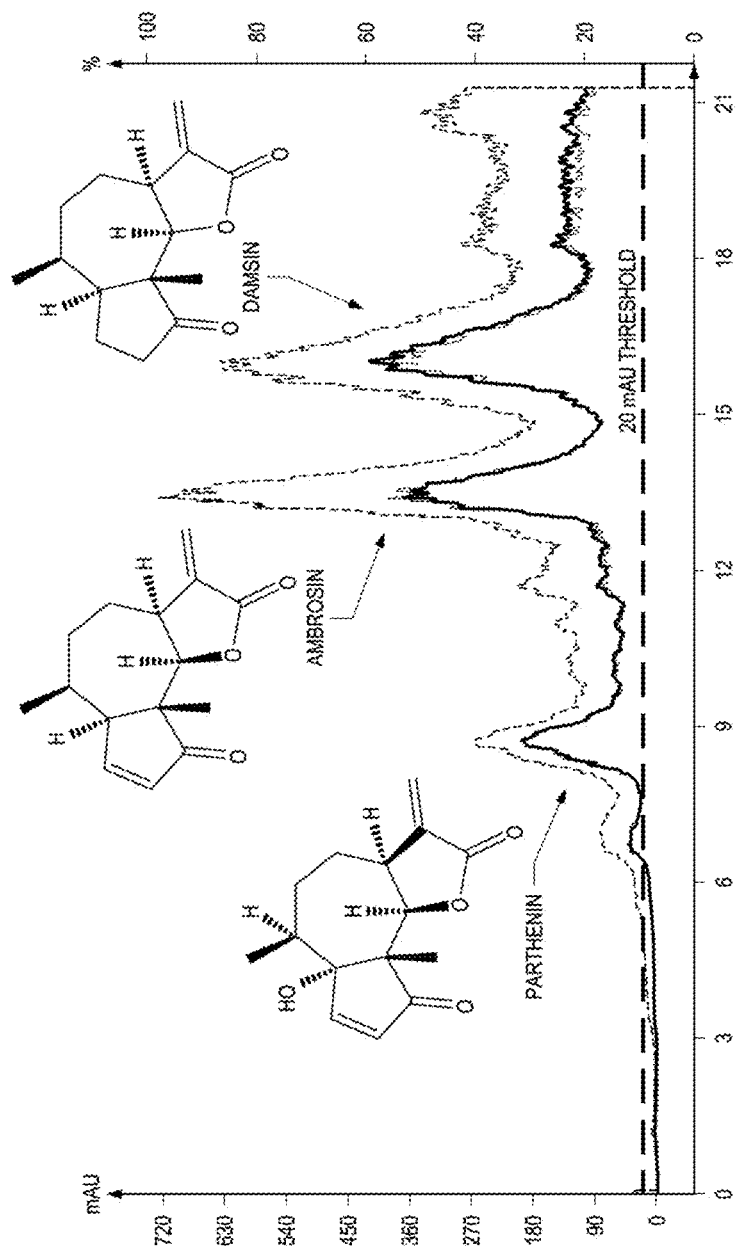
FIG. 1C. Chromatographic fingerprints of sesquiterpene lactones extracted from *Ambrosia maritima*.
Figure 1D:
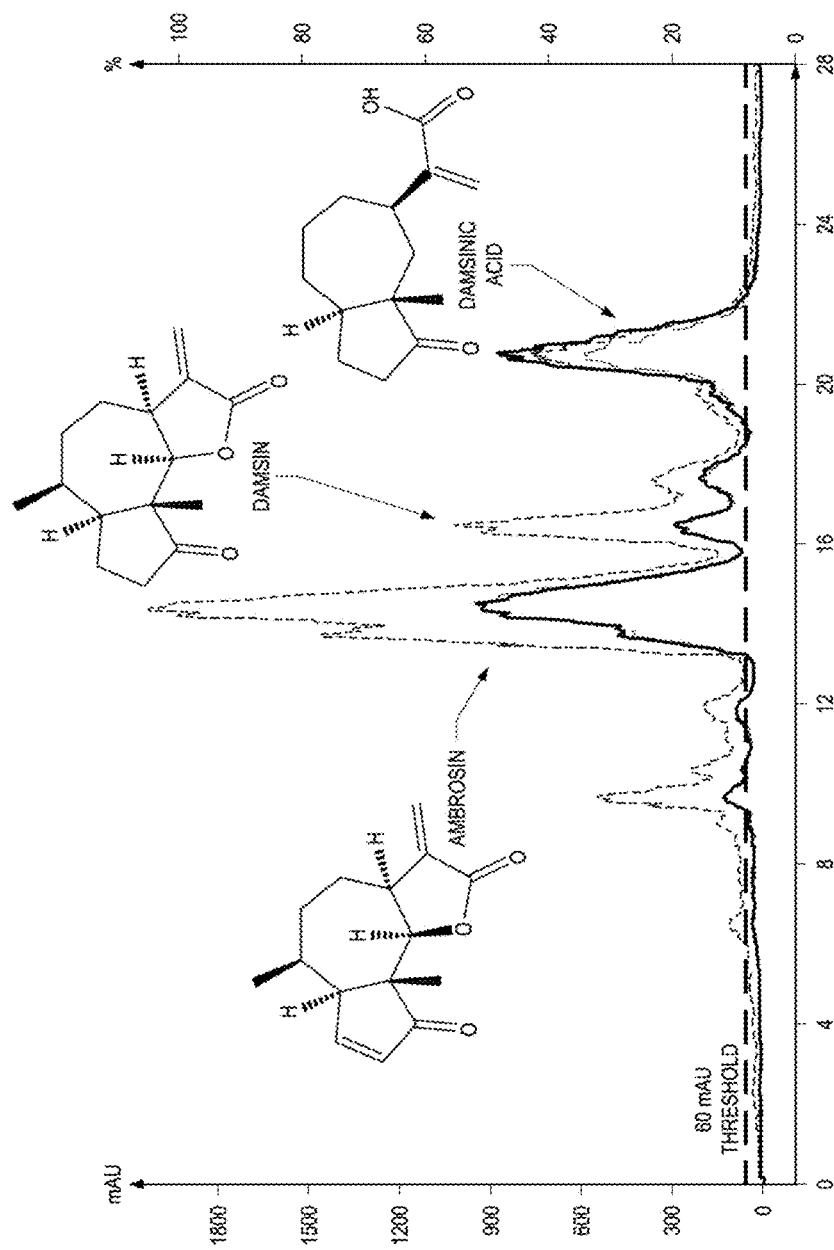
FIG. 1D. Chromatographic fingerprints of sesquiterpene lactones extracted from *Ambrosia hispida*.

The invention provides plant based compounds and novel methods pertaining to their use in cancer treatments. In particular, the organic extract from *Ambrosia maritima* and/or *Ambrosia hispida* plants in the Asteraceae family is used for treatment of various cancers. One particular group of components in the organic extract, sesquiterpene lactones, have been found to interfere with a variety of molecular signal pathways in cancer progression and to reduce the tumor(s), thus enabling effective cancer treatment. Further, the organic extract can be combined with other cancer fighting compounds or therapeutics that address other signal pathways for a more complete treatment.

The present methods includes any of the following embodiments in any combination(s) of one or more thereof:

A method of treating cancer, comprising administering an effective amount of a composition comprising an organic extract of *Ambrosia maritima* or *Ambrosia hispida*, together with a pharmaceutically acceptable carrier to a patient with cancer. In particular, the cancers are bladder cancer, prostate cancer, triple negative breast cancer, lung cancer and pancreatic cancer. The effective amount of the composition is administered daily for at least 6 weeks. Further, the organic extract comprising at least one sesquiterpene lactone is protein free, thus is less pyrogenic.

A method of treating cancer, comprising administering an effective amount of a composition comprising sesquiterpene lactones extracted from *Ambrosia maritima* or *Ambrosia hispida* together with a pharmaceutically acceptable carrier to a patient with cancer. In particular, the cancer is bladder cancer, prostate cancer, or triple negative breast cancer and the effective amount of the composition is administered daily for at least 6 weeks.

A method of reducing cancer metastasis comprising administering an effective amount of a composition comprising sesquiterpene lactones extracted from *Ambrosia maritima* or *Ambrosia hispida* together with a pharmaceutically acceptable carrier to a patient with cancer.

A method for enhancing the inhibition of p65, STAT3, GPR30, EGFR family of receptors, β-catenin pathway and Rho-GTpase family activity in a patient, comprising administering an effective amount of a composition comprising sesquiterpene lactones extracted from *Ambrosia maritima* or *Ambrosia hispida* together with a pharmaceutically acceptable carrier to a patient.

A method of preparing a sesquiterpene lactone-containing extract for pharmaceutical involving treating an *Ambrosia maritima* plant with an organic solvent in which at least one said sesquiterpene lactone is soluble, evaporating the organic solvent to produce a crude extract, running or passing the crude extract through a chromatographic separation using a second organic solvent to obtain a clean extract of the sesquiterpene lactone(s), and collecting fractions of the individual sesquiterpene lactone(s).

A method of preparing a sesquiterpene lactone-containing extract for pharmaceutical involving treating an *Ambrosia hispida* plant with an organic solvent in which at least one said sesquiterpene lactone is soluble, evaporating the organic solvent to produce a crude extract, running or passing the crude extract through a chromatographic separation using a second organic solvent to obtain a clean extract of the sesquiterpene lactone(s), and collecting fractions of the individual sesquiterpene lactones.

The sesquiterpene lactones (SLs) in the present methods can be used to target a variety of cancer-specific signal pathways. The examples below demonstrate the effect of SLs on cancer cell proliferation pathways (i.e. NF-κB and STAT3) and promoting apoptotic cell-death pathways (i.e. Caspases 3, 7, and 6) and its interactions with G protein coupled receptors. However, it is expected that SLs can also affect other signal pathways and the examples should not be construed as to limiting the mechanisms by which the SL affect cancer.

Once the proof of concept of the SL affecting various cancer-specific signal pathways was determined, a series of in vitro experiments using bladder cancer cell lines, breast cancer cell lines, and prostate cancer cell lines were performed to prove efficacy.

Not all signal pathways involved in cancer formation, growth, and progression are known. Thus, the following examples are intended to be illustrative only, and not unduly limit the scope of the appended claims. Further, though on a limited number of cancer cell lines were utilized, the present treatment methods are expected to be useful for treatment of most cancers, either alone or in combination with other treatment modalities.

EXTRACTION METHOD

Briefly, the extraction uses an organic solvent such as methanol, ethanol and any carbon based solvents. The whole organic extract would be dried and chemically fractionated with chloroform. The final step is to pool the best fractions and evaporate the chloroform. The final product can then be used in treatment.

In more detail, the extraction method of *Ambrosia maritima* can be as follows:

1) Dried whole *Ambrosia maritima* plant is powdered using conventional means.

2) The powdered plant is brought into contact with an organic solvent or combination of organic solvent and allowed to contact for a predetermined amount of time for the SLs in the dried plant to move into the organic phase.

3) The organic solvent(s) is then separated from the dried plant material.

4) The organic extract is dried by any known means in the art.

5) The dried extract is chemically fractionated with chloroform and fractions rich in the requisite SLs pooled.

6) The chloroform is evaporated, leaving behind the dried, pharmaceutically active components.

7) Different concentrations of the active components are used in treating various cancer cell lines.

The same extraction steps can be performed for *Ambrosia hispida* and other plants in the plants in the Asteraceae family.

Other extraction methods can be employed, as suitable for organic soluble components. For example, such methods include, aqueous two-phase systems, acid/base extractions, and the like. To prepare the plant for extraction the plant should be dried in air with no heat then could be further processed by freeze thawing cycles, and/or physically lysed by freezing and thawing before extraction, and the like.

The active ingredient or ingredients of the organic extract of the plant material can combined with other active ingredients before use, but preferably are used alone. The active ingredient or ingredients of the organic extract of plant material can be used as is, or can be formulated with known pharmaceutically acceptable carriers, diluents and/or excipients.

For example, gelatin capsules containing dried organic extract can be produced containing a suitable dose of the active ingredient(s). Optionally, packets containing the dried extract can be provided for mixture with e.g., hot fluids, to be taken orally. The extract can also be formulated with solid carriers for pressing into pill forms, especially with delayed release excipients for formulating once a day tablet forms or any pharmaceutical form that will be orally administered.

It may also be possible to prepare forms of the active ingredients suitable for non-oral routes of administration, such as inhalational, buccal, sublingual, nasal, suppository or parenteral dosage forms.

The above extract is significantly more stable than the natural product, even in liquid form and especially when formulated with a buffer and a chelator. It is also significantly more concentrated than the natural form, thus providing efficacy without having to consume vast quantities of plant material. Further, the dosage is much more easily controlled with concentrated, partially purified or purified material.

We also used TLC and HPLC to further purify the active ingredient(s) to be further studied and to determine their efficacy, although this work is ongoing. The removal of certain components from the organic extract, through the additional purification step can lead to fewer side effects. *Ambrosia maritima* and *Ambrosia hispida* are ragweed, which is known for its allergenic effects. Thus, purification of the organic extract will lead to a reduced immune response in humans. In some embodiments, purified material from the organic extract of the *Ambrosia maritima* and *Ambrosia hispida* can serve to improve the ability to interrupt signal pathways in cancer cells and increase stability of the extracted material.

NF-KAPPA B PATHWAY

The common molecular mechanisms of cancer growth include:
  Self-sufficiency in growth and loss of growth inhibitor mechanisms
  Suppression of apoptotic threshold
  Enhanced angiogenic properties
  Ability to invade local tissue and metastasize to different sites Each of these cellular processes is known to be affected by the NF-κB pathway. NF-κB is a protein complex widely used by eukaryotic cells as a regulator of genes that control cell proliferation and cell survival. In mammalian cells, the NF-κB family is composed of five members: RelA (p65), RelB, c-Rel, p50/p105 (NF-κB1) and p100 (NF-κB2). Under most basal conditions NF-κB complexes are maintained in an inactive form primary through interactions with the inhibitor of κB (IκB) family of proteins. Cancer, however, is a disease that stems from diverse etiologies that harbor distinct affected cell targets, therefore shows a very complex nature. In cancerous cells proliferation and homeostasis are greatly altered. Thus, the NF-κB complexes become quickly misregulated. As such, many different types of human tumors have misregulated NF-κB: that is, NF-κB is constitutively active. One important area of cancer research is focused on targeting the constitutively active NF-κB in cancer cells.

The sesquiterpene lactone-containing organic extracts from the *Ambrosia maritima* were tested to determine the effects, if any, on the NF-κB pathway. Looking at computational docking analysis, there was a potential binding site. The binding site was was confirmed by western blotting where we observed an inhibition of p65 (RelA) within 30 minutes of treating the cells.

Figure 2A:
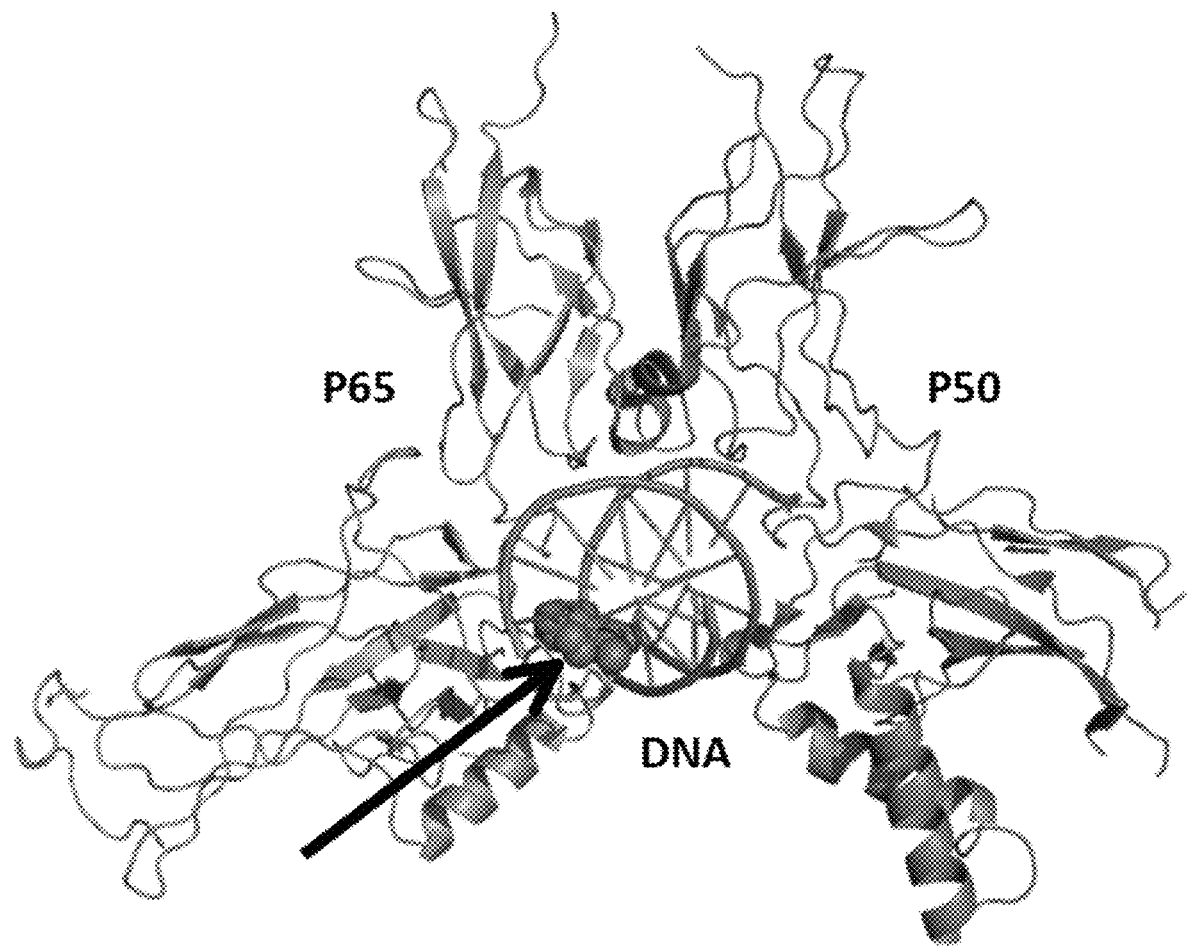
FIG. 2A shows the binding of Ambrosin and the inhibition of p65 subunit of Nf-kappa-B to disrupt the Nf-kappa-B/DNA interaction.
Figure 2B:
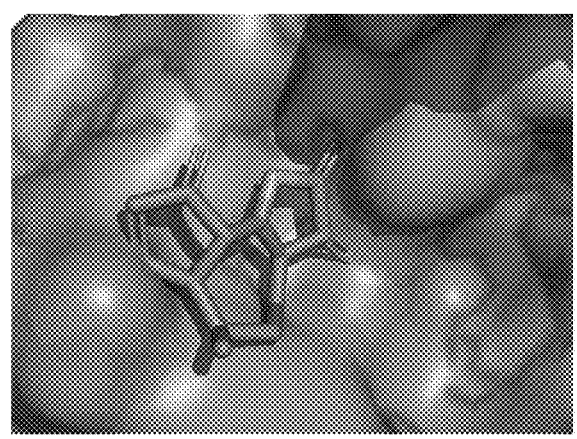
FIG. 2B shows another view of the Ambrosin binding to NF-κB DNA docking domain at Cys122 and Cys 207.
Figure 2C:
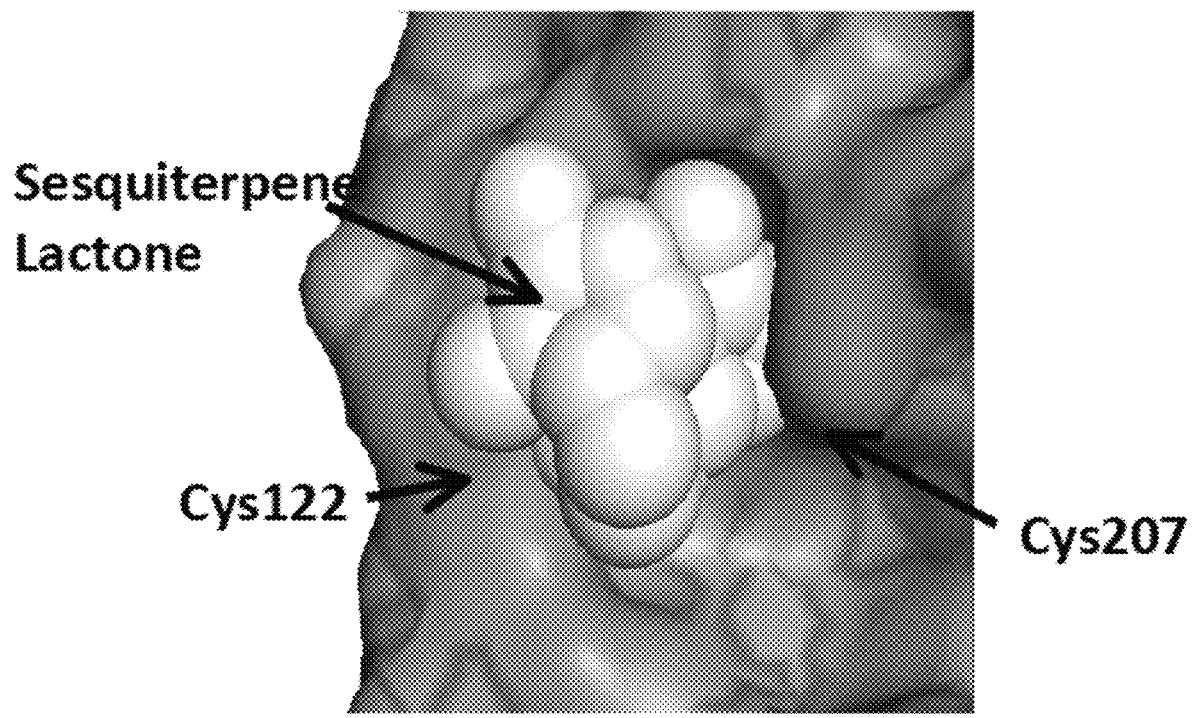
FIG. 2C shows the Ambrosin (cluster of spheres) binding to NF-κB DNA docking domain at Cys122 and Cys 207.
Figure 2D:
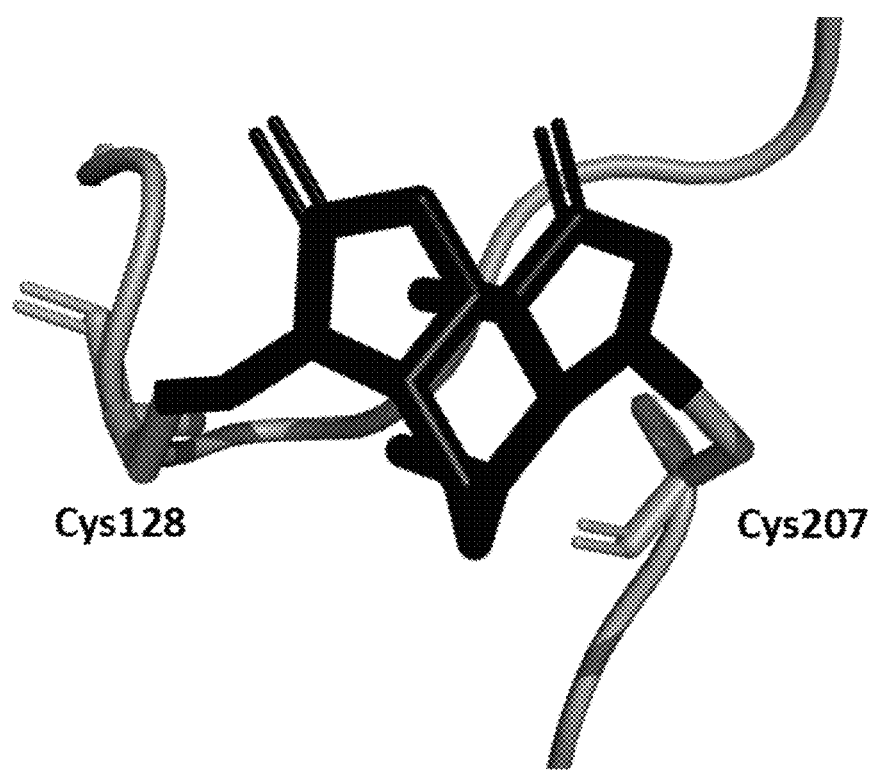
FIG. 2D shows a second view of the sesquiterpene lactone binding to NF-κB P65.

FIG. 2A-D displays the binding prediction of one sesquiterpene lactone, Ambrosin, to the NF-κB/DNA binding domain. The arrow in FIG. 2A shows that the Ambrosin (cluster of spheres) can bind with the NF-κB to disrupt its bind to DNA (helical structure in center of diagram) at the P65 unit. Because of the two Michael reaction sites, this sesquiterpene lactone is expected to bind to the Cys 122 and Cys 207 on the NF-κB structure, as shown in FIGS. 2B and 2C. By binding to one or both in a selective binding way, the Ambrosin blocks these cysteines and the NF-κB is no longer available as a transcription factor for DNA binding, thus slowing the progression of the tumor.

The ability of a sesquiterpene lactone to block the NF-κB/DNA binding was tested using four bladder cancer cell lines: UM-UC-6 (H. B. Grossman University of Texas M. D. Anderson Cancer Center), UM-UC-9 (H. B. Grossman University of Texas M. D. Anderson Cancer Center), UM-UC-10 (H. B. Grossman University of Texas M. D. Anderson Cancer Center), SW-780 (ATCC).

Figure 3:
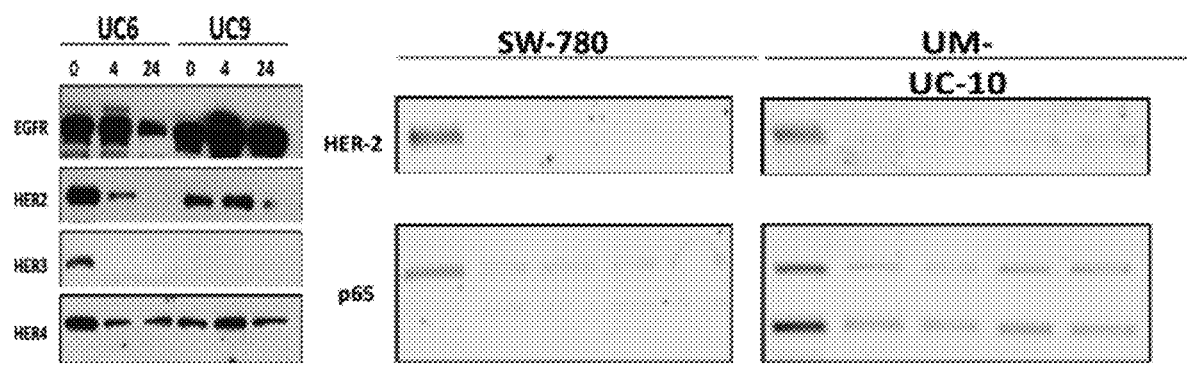
FIG. 3 displays gel electrophoresis (western blots) showing the results of sesquiterpene lactones (50 μg/mL) inhibition of the important cancer related members of ErbB Family as well as p65 expression in multiple bladder cancer cell lines.

FIG. 3 displays the gel electrophoresis results for 50 µg/mL of sesquiterpene lactones, extracted from *Ambrosia maritima*, on UM-UC-6, UM-UC-9, UM-UC-10, and SW-780 cell lines. The sesquiterpene lactones inhibited EGFR, HER-2, HER-3 in all four bladder cancer cell lines. Of particular importance is the inhibition of HER-2. HER-2 is one of the transcriptional target genes of p65 NF-κB. Its inhibition by the addition of the organic extract containing sesquiterpene lactones confirms the ability to disrupt NF-κB/DNA binding and substantiates the proposed mechanism in FIG. 2. Thus, the SLs inhibit the EGFR family of receptors.

STAT3

Normal cellular responses to cytokines, growth factors and other polypeptide ligands are mediated by a family of latent cytoplasmic transcription factors called Signal Transduction and Activator of Transcription (STAT). Aberrant STAT3 leads to the induction of cellular and biological processes including proliferation, differentiation, survival, development, inflammation, invasion and metastasis in cancer.

Many human malignancies had been shown to harbor constitutively active STAT3 that contribute to many cellular and biological processes within the cancer cells.

By targeting and inhibiting the DNA-binding domain of STAT3, we can inhibit the transcriptional activity of STAT3. Physical interaction of STAT3/DNA binding domain with the consensus DNA-binding sequence in the promoter region of responsive genes is a very important step for STAT3 function. The disruption of the protein DNA interactions by sesquiterpene lactones has the potential to inhibit STAT3-dependent gene transcription blocking its tumor promoting functions.

Figure 4A:
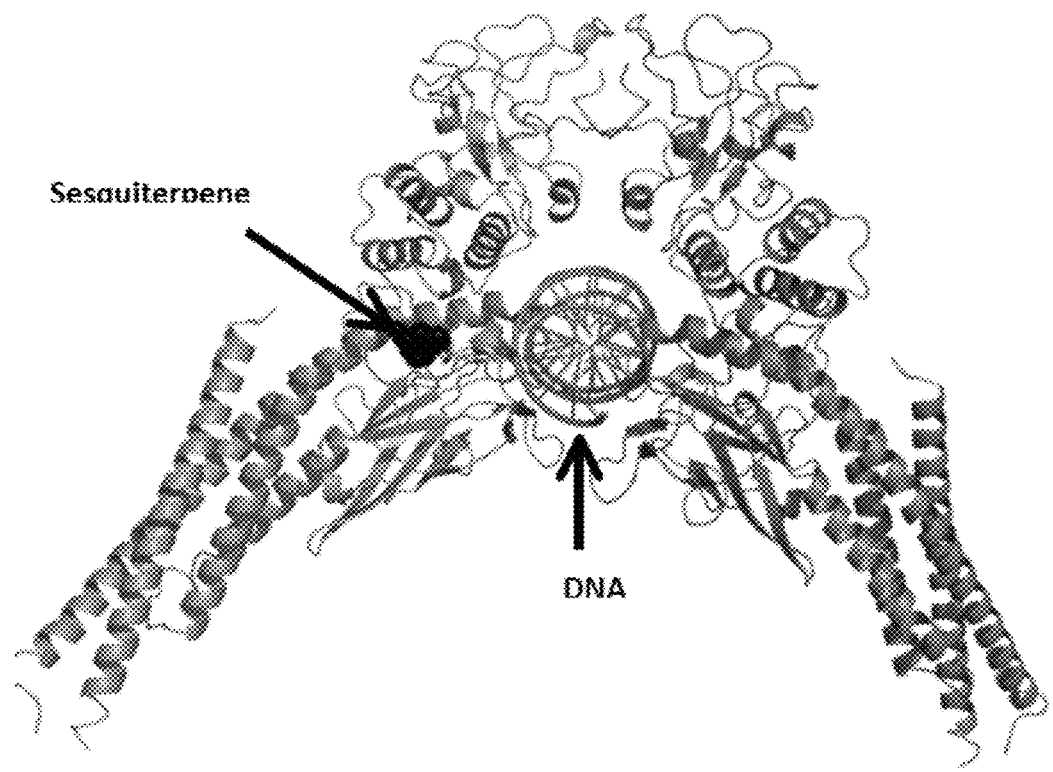
FIG. 4A shows the binding of one of the sesquiterpene lactones (spheres) to STAT3 to disrupt its binding to DNA. The sesquiterpene lactone Ambrosin binds the Cys 251 and Cys 328.
Figure 4B:
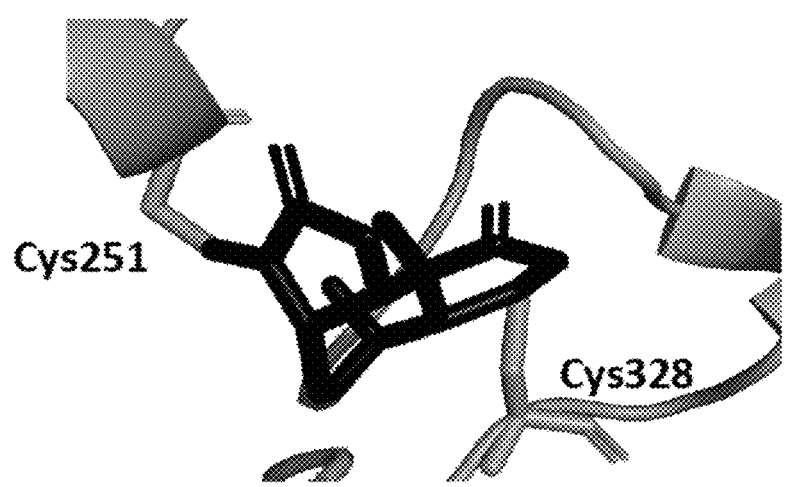
FIG. 4B displays a close up of the binding region in FIG. 4A.

FIG. 4A-B shows a proposed mechanism by which the extracted sesquiterpene lactones may link the Cys 328 and Cys 251 on the DNA binding domain of the STAT3. This linkage would block the binding of DNA and disrupt transcription, thus slowing growth of the cancer.

Using protein kinase arrays, STAT3, STAT5 and STAT6 were all determined to be affected by treatment of the cells with SLs extracted from *Ambrosia maritima*. More tests will be performed to show that SLs can disrupt STAT3/DNA binding.

CASPASE STABILITY

Apoptosis or controlled cell death occurs in response to many different environmental stimuli or because of disease conditions. During apoptosis, morphological and biochemical changes trigger the breakdown of cellular processes and compartments. Defective apoptosis represents a major causative factor in the development and progression of cancer. Further, the ability of tumor cells to evade engagement of apoptosis can play a significant role in their resistance to conventional therapeutic regimens.

One of the most conserved biochemical features of apoptotic cell death is the activation of caspases. Caspases (cysteinyl-directed aspartate-specific proteases) are a family of highly specific proteases that play a key role during the apoptotic cell death. Caspases are grouped as either initiators or effectors of apoptosis, depending on where they enter the cell death process. The initiator caspases are present as monomers (i.e. inactive pro-forms) that must dimerize for full activation whereas effector caspases are present as dimeric zymogens that must be processed for full activation. Once activated, the effector caspases cleave other zymogen protein substrates within the cell, to trigger a cascade of caspase being activated and the apoptotic processe.

Caspase-3 and Caspase-7 are the major apoptotic executioner proteases and directly cleave most of the proteins that are proteolyzed during apoptosis. The effector caspase-3 and caspase-7 homodimers are activated by 2 protease 'nicks', producing an active tetrameric form with a 20 kDa and a 10 kDa chains. Stabilization of this tetramer promotes apoptosis.

Figure 5A:
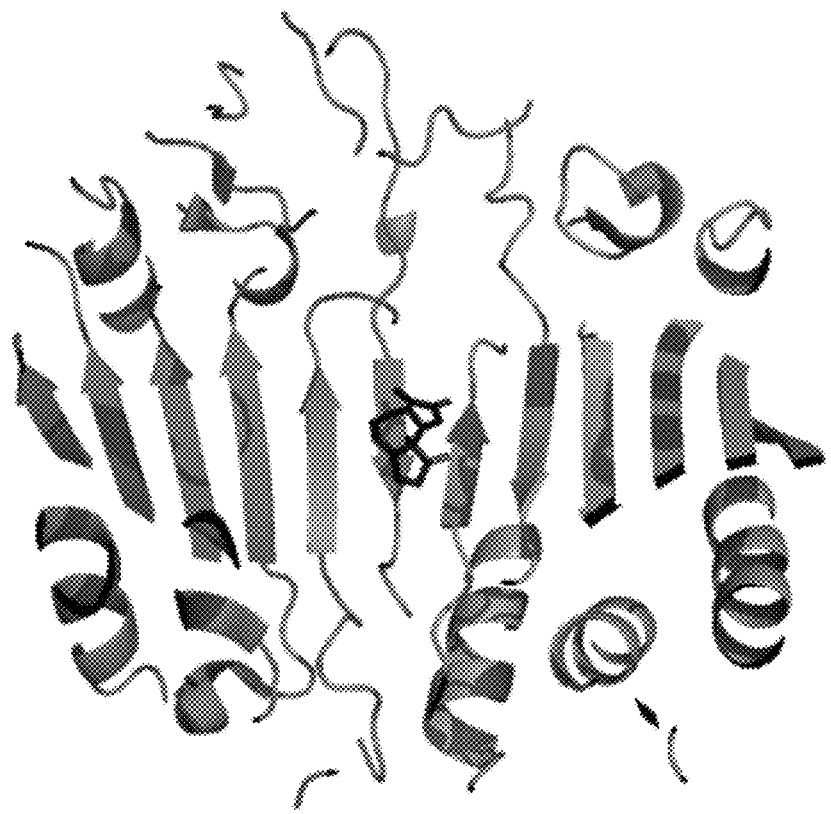
FIG. 5A displays the sesquiterpene lactone Ambrosin linking the two Caspase-7 homodimers. A close up of the interaction with symmetry related Cys290 and Cys 290' side chains leading to the stabilization of the homodimer is show in FIG. 5B.
Figure 5B:

SLs are able to stabilize the tetramer structure by forming a covalent crosslink across the molecular two-fold axis of symmetry. FIG. 5A displays Ambrosin linking the two Caspase-7 homodimers at Cys 290 and Cys 290'. A close up of this linkage is shows in FIG. 5B. The interaction of the Ambrosin with the tetramer in these molecular models was confirmed by computational docking.

Without the SLs stabilizing the activated tetramers of Caspase-3 and Caspase-7, the tetramers would fall apart and be proteolyzed within 15-30 minutes, thus disrupting the apoptosis procedure. With the SL linkage, the tetramers are stable indefinitely in the active form and apoptosis proceeds as usual.

G-Protein Coupled Receptor 30 (GPR30)

The effects of all hormones, including steroids such as estrogen, are mediated by specific receptors that recognize and bind the hormone transmitting this information to downstream effectors. In triple negative breast cancer (TNBC) tumors, estrogen receptor α (ER-α) and progesterone receptors are non-expressed and the Her/2neu gene is under expression. This makes it more difficult to treat since most chemotherapies target one of the three receptors, thus this class of breast cancer is not susceptible to endocrine therapy. Patient mortality with TNBC is double the mortality rate of ER-a positive tumors. Hence, there is an urgent necessity for developing an innovative pharmacological targeted therapy for TNBC patients.

In recent years, a large number of reports have described membrane-associated estrogen receptors, either similar to or distinct from the classical nuclear estrogen receptors. These receptors have been postulated to mediate aspects of cellular estrogen function, including traditional genomic (transcriptional) signaling as well as novel non-genomic (rapid) signaling.

Estradiol, or more precisely, 17β-estradiol, is a human sex hormone and steroid, and the primary female sex hormone. Most non-genomic rapid signaling events of 17β-estradiol are due to G-protein coupled receptor 30 (GPR30). GPR30 in highly expressed and prevalent in TNBC and is associated with high recurrent and mortality rate of TNBC. The binding of GPR30 with 17β-estradiol increases TNBC cell proliferation. Potent inhibitors that binding, targeting and inhibiting GPR30 are needed in TNBC treatment to block this receptor from binding to its ligand.

Molecular docking, a common computational tool for calculating binding affinities and predicting mode and binding sites, was performed on the ability of SLs to bind to the GPR30 receptor and prevent the reception of 17β-estradiol. The molecular docking predicting the binding of sesquiterpene lactones to GPR30 at Cys-205 and Cys-130. Similar to the crosslinking of the two cysteine residues on STAT3, SLs are expected to bind both of these sites on the GPR30 and prevent the docking of the 17β-estradiol. In practice, this will decrease the TNBC cell proliferation.

Figure 6A:
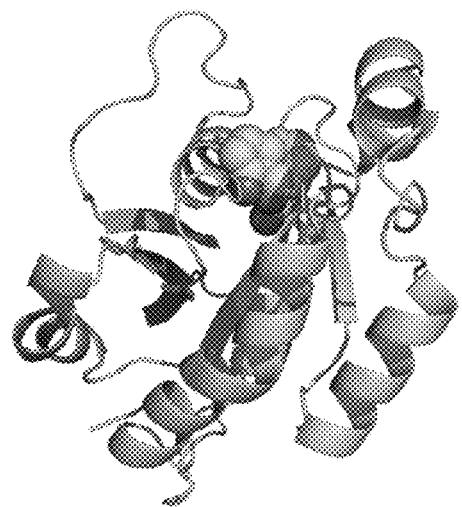
FIG. 6A displays a sesquiterpene lactone linking the GTP binding site of Rho family GTPases. A close up of this linkage showing the SL binding to the Cys 157 and Cys 18 is show in FIG. 6B.
Figure 6B:
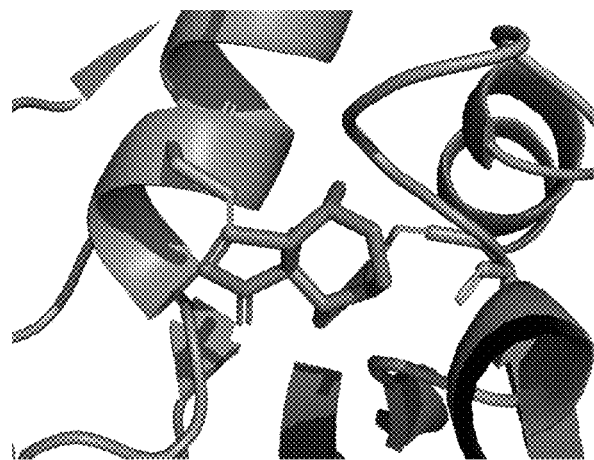

Additionally, the Rho family of GTPases is a family of small (~21 kDa) signaling G proteins. The human Rho family of GTPases includes CDC42, RhoA, and Rac1. These proteins function to regulate cell migration, endocytosis, and cell cycle progression in normal cells. Disregulation of these critical regulatory proteins through the interaction with the Dbl onco-protein product leads to oncogenic cell transformation. Our molecular docking calculations strongly suggest that our plant derived sesquiterpene lactones can bind specifically adjacent to the GTP binding site of Rho family GTPases, thus displacing GTP and inactivating the enzyme (FIGS. 6A and 6B). This would effectively block the proliferation and migration of bladder, prostate and breast cancer cells upon treatment with the sesquiterpene lactones.

IN VITRO RESULTS

In vitro experiments were performed with multiple bladder and prostate cancer cell lines, which are shown in Table 1.

TABLE 1

Abbreviations of Cell lines

| Cell Lines | Abbreviation |
| --- | --- |
| Bladder cancer cell line (ATCC, Manassas, VA) | J82 |
| Bladder cancer cell line (ATCC, Manassas, VA) | T24 |
| Bladder cancer cell line (H. B. Grossman, University of Texas, M. D. Anderson Cancer Center, Houston TX) | UM-UC-10 |
| Bladder cancer cell line (ATCC, Manassas, VA) | SW780 |
| Bladder cancer cell line (ATCC, Manassas, VA) | 5637 |
| Bladder cancer cell line (H. B. Grossman, University of Texas, M. D. Anderson Cancer Center, Houston TX) | UM-UC-9 |
| Lymphatic metastasis of prostate cancer (ATCC, Manassas, VA) | LNCaP |
| Bone metastasis of prostate cancer (Sellers, Dana-Farber Cancer Institute, Boston, MA) | C4-2B |
| Primary prostate cancer cell line (ATCC, Manassas, VA) | PC-3 |
| Bladder cancer cell line (ATCC, Manassas, VA) | RT4 |
| Bladder cancer cell line (H. B. Grossman, University of Texas, M. D. Anderson Cancer Center, Houston TX) | UM-UC-14 |
| Bladder cancer cell line (H. B. Grossman, University of Texas, M. D. Anderson Cancer Center, Houston TX) | UM-UC-5 |
| Breast cancer cell line (ATCC, Manassas, VA) | SUM159 |
| Breast cancer cell line (ATCC, Manassas, VA) | MDA-MB-231 |
| Breast cancer cell line (ATCC, Manassas, VA) | MDA-MB-474 |
| Breast cancer cell line (ATCC, Manassas, VA) | MDA-MB-468 |

SLs in varying concentrations were added to the cell lines and the results were tabulated at 48 hours. For SL concentrations below 0.08%, DMSO was used to dissolve the compounds.

Figure 7:
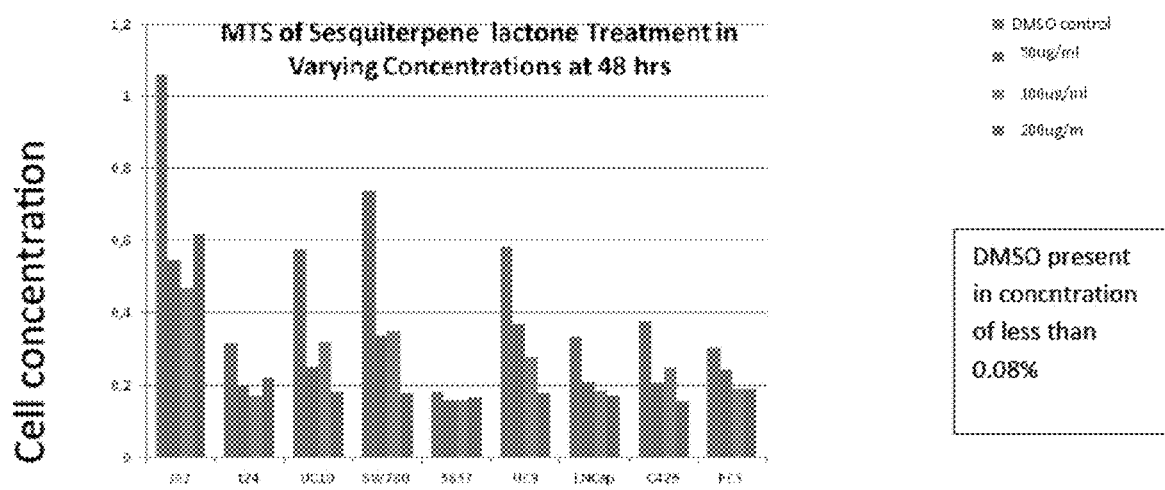
FIG. 7 displays cell concentration as assayed by MTS for various cancer related cell lines after exposure to various concentrations of the sesquiterpene lactones extracted from the *Ambrosia maritima* plant.

First, the cell viability was tested using an MTS assay and 50, 100, and 200 μg/mL of SLs concentrations extracted from *Ambrosia maritima*, the results of which are shown in FIG. 7. All cell lines showed a significant decrease of cell viability in the SLs treated cells in comparison to the DMSO control cells. The concentration of DMSO used to dissolve SLs and in the control did not exceed 0.08%.

Figure 8:
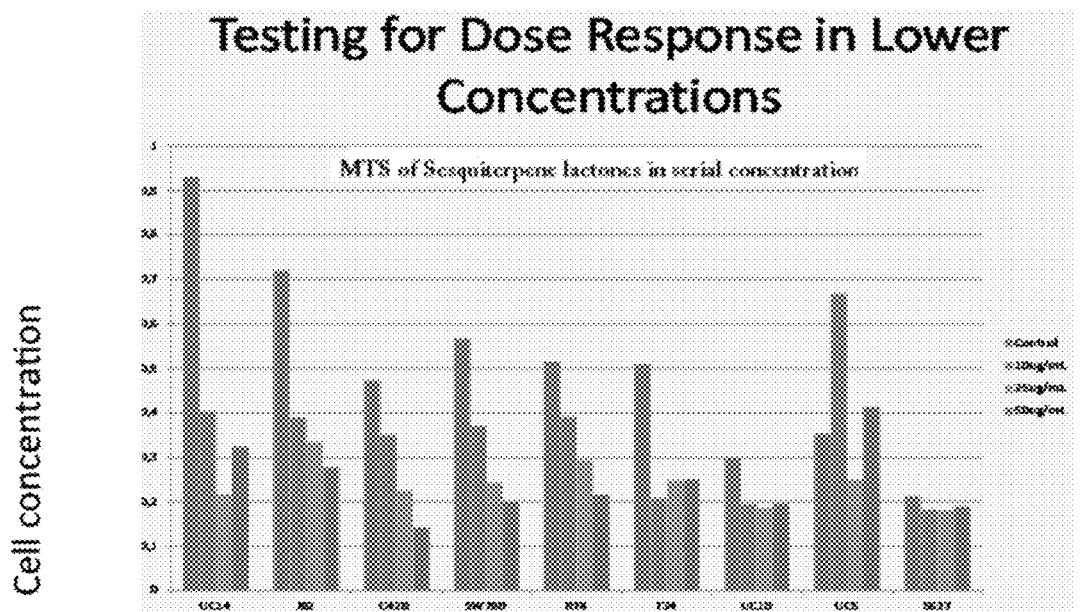
FIG. 8 displays cell concentration as assayed by MTS for various cancer related cell lines after exposure to low concentrations of sesquiterpene lactones extracted from the *Ambrosia maritima* plant.
Figure 9:
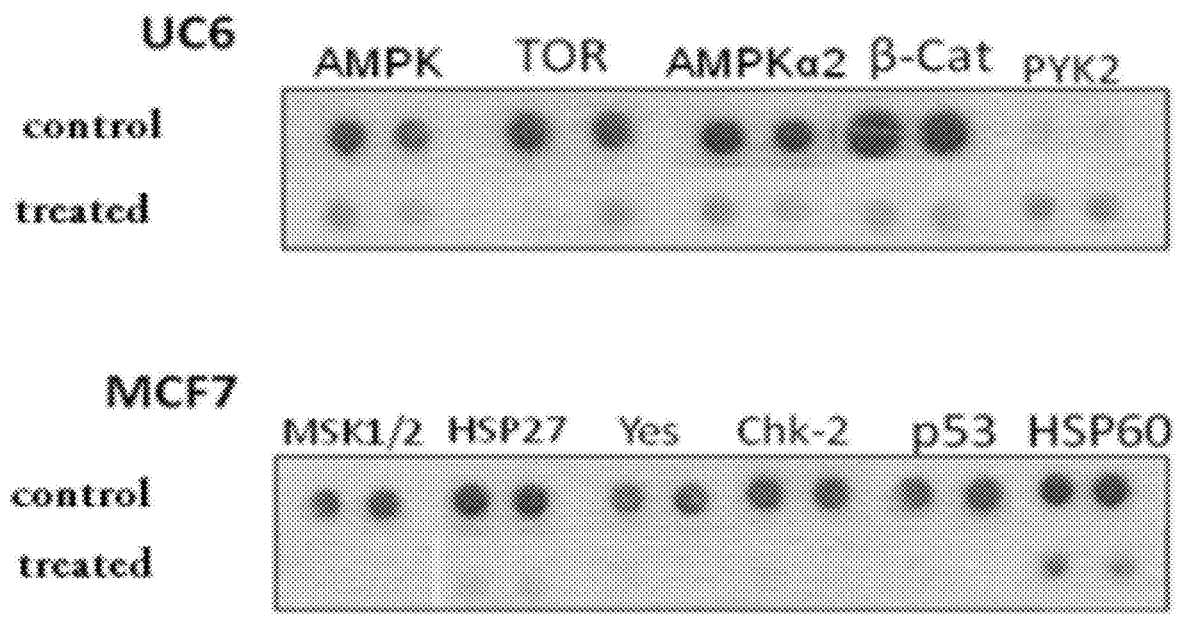
FIG. 9 displays a phosphokinase array that illustrates the effect of 25 μg/mL of the sesquiterpene lactones extracted from *Ambrosia maritima* on cancer related signaling proteins in UM-UC-6 bladder cancer and MCF7 breast cancer.

Lower concentrations of the SLs (10, 25 and 50 μg/mL) were tested against multiple bladder cancer cell lines was tested for efficacy. FIG. 8 displays these results. At reduced concentrations of sesquiterpene lactones, the cells responded by exhibiting lower viability by MTS even at the lowest concentration of 10 μg/mL. FIG. 9 is a phosphokinase array that illustrates the effect of 25 μg/mL SL on cancer related signaling proteins in UM-UC-6 bladder cancer and MCF7 breast cancer. The phosphokinase array shows that the cell that had been treated with a concentration of 25 μg/mL of SLs for a 3-hour treatment duration caused the inhibition of important signaling and energy proteins that are important in cancer cell survival, such as AMPK, TOR, beta-Cat and the like. The results of the phosphokinase array are also important in that they substantiate the proposed binding predictions in FIG. 2 et seq.

IN VIVO RESULTS

Figure 10:
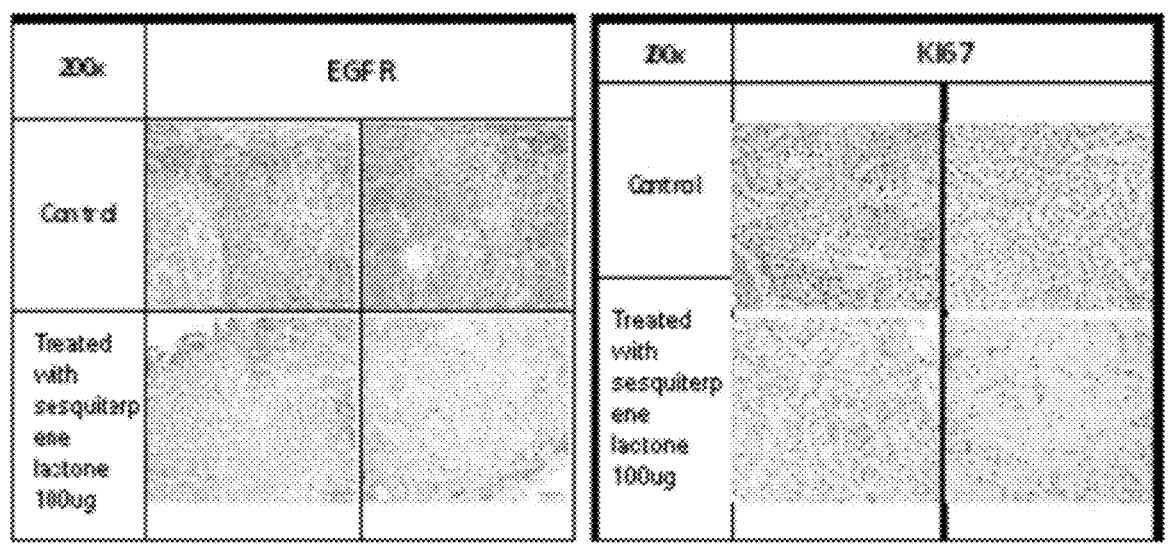
FIG. 10 displays histopathology of Epidermal Growth Factor Receptors and Ki-67 in control mice xenografted with UM-UC-6 cells and mice injected with UM-UC-9 cells but treated using sesquiterpene lactones extracted from *Ambrosia maritima*. The concentration of the sesquiterpene lactones were 100 μg/dose.

Thirty NOD-SCID mice were injected subcutaneously with 1 million UM-UC-6 cells. One week post injection, and after establishment of the tumor, a daily treatment with 4 μg/g of SLs was started. The animals were sacrificed 6 weeks after the beginning of the daily treatments. The histopathology of the xenografted treated and control animals showing the amount of epidermal growth factor receptor (EGFR) and Ki-67 are shown in FIG. 10. EGFR is important in cancer progression and Ki-67 is indicative of mitotic activity. Here, the EGFR and Ki-67 were less in the treated animals. This indicates that cancer progression is inhibited by SLs daily treatment and there was less mitotic activity and less proliferation of the cancer.

Additional in vivo experiments were conducted for three breast cancer cell lines that were orthotopically injected into mice. Orthotopic injection of breast cancer cells is a powerful model to study all aspects of cancer growth. One million cells of each MDA-MB-231, SUM-159 and MDA-MB-468 were injected into the mammary fat pad of mice to form tumors. Once tumors were established, the tumors were treated with the SL-containing organic extraction of *Ambrosia maritima* at a dose of 200 μM of total SLs/animal daily.

Figure 11A:
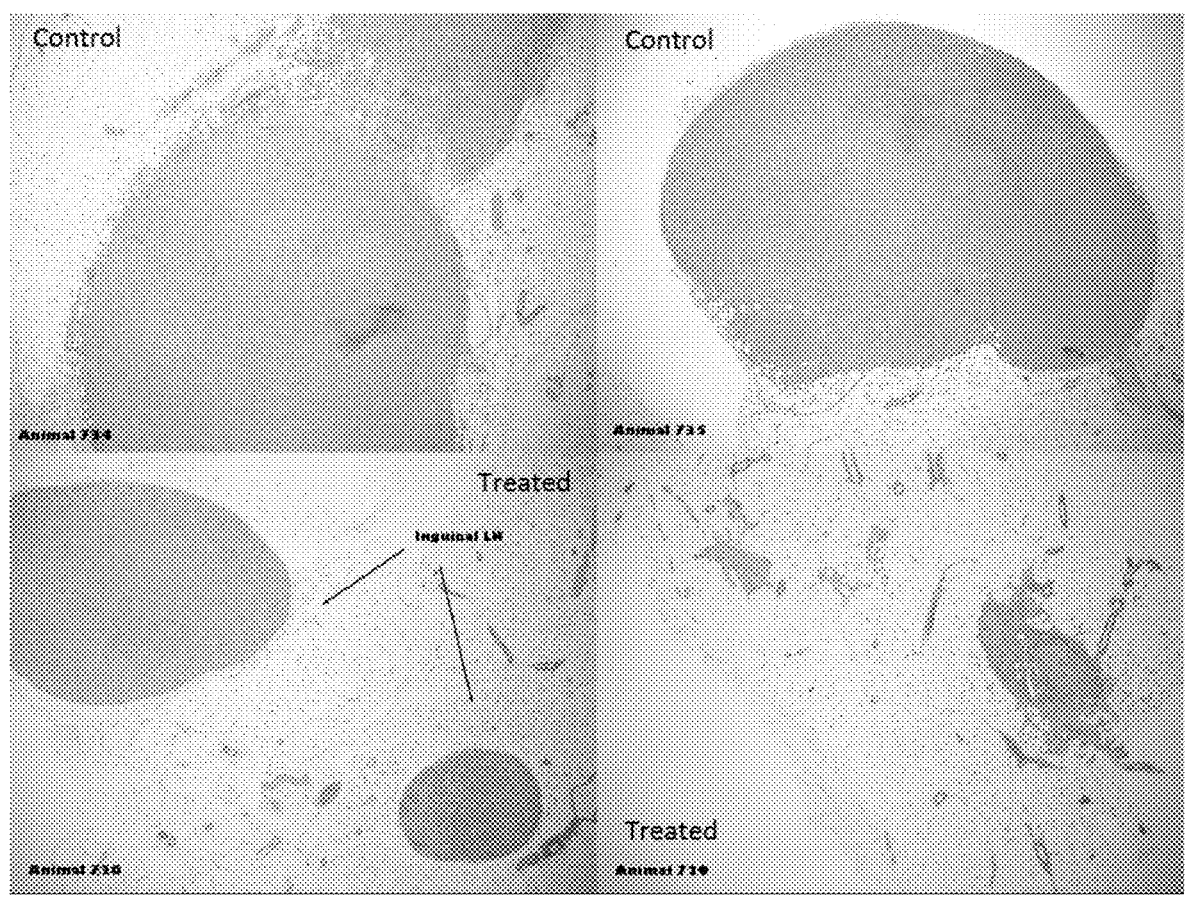
FIG. 11A displays histopathology of orthotopically injected SUM-159 breast cancer cells in control mice (top) and mice treated with sesquiterpene lactones extracted from *Ambrosia maritima*.
Figure 11B:
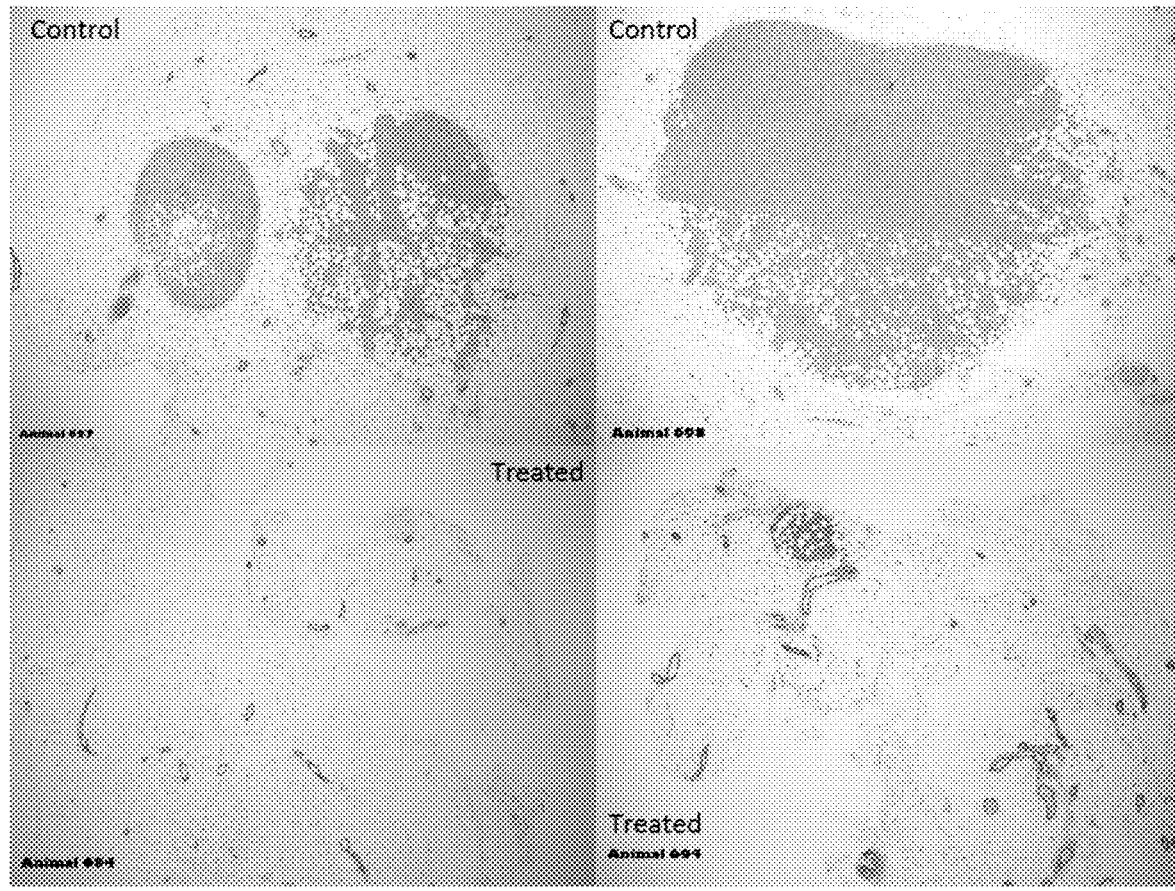
FIG. 11B displays histopathology of orthotopically injected MDA-MB-231 breast cancer cells in control mice (top) and mice treated with sesquiterpene lactones extracted from *Ambrosia maritima*.

FIGS. 11A-B show the histopathology of the tumor area in the mice treated with the SLs extracted from *Ambrosia maritima* versus control animals for the SUM-159 and MDA-MB-231 cell lines. These results showed that the tumor size is smaller in the animals treated with SLs than the control.

Figure 11C:
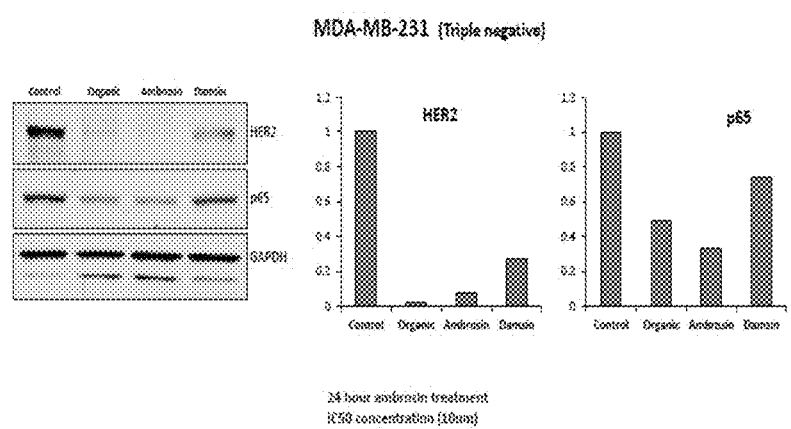
FIG. 11C displays results for orthotopically injected MDA-MB-231 triple negative breast cells treated with an organic extract containing all sesquiterpene lactones from *Ambrosia maritima*, purified sub fractions containing Ambrosin only, and purified sub fractions containing Damsin only.

FIG. 11C shows the results of the level of expression of HER2 and p65 in xenografted animals with MDA-MB-231 triple negative cell line and the corresponding bar graph that shows that inhibition for the control animals and animals treated with the SL organic extract, Ambrosin-only purified extract, and Damsin-only purified extract. The largest decrease of HER2 and p65 was seen with the SL organic extract, but significant improves were also seen with Ambrosin and Damsin only treatment. Thus, these components can be purified individually from the SL organic fraction and then combined as a potential treatment.

Figure 12:
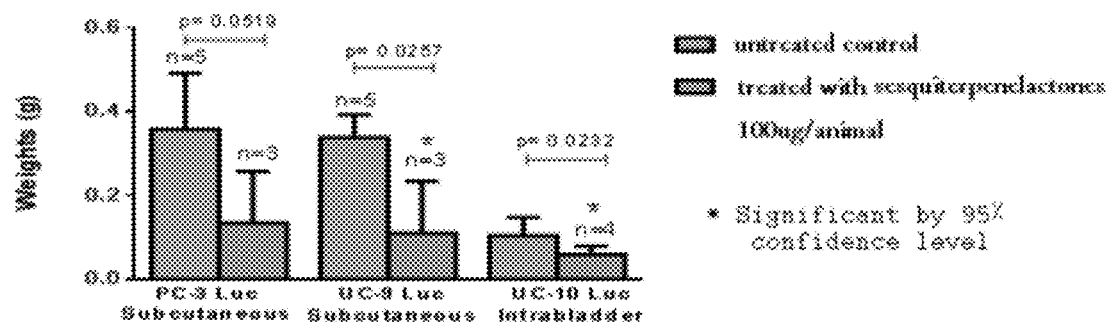
FIG. 12 displays results of tumor weight of mice xenografted with $PC-3^{LUC}$, $UM-UC-9^{LUC}$, or $UM-UC-10^{LUC}$ bladder cell lines with and without daily sesquiterpene lactones treatment.

A comparison of tumor size for three different Luciferase-labeled cell lines were also performed and the results are shown in FIG. 12. In this series of experiments, the PC-3$^{LUC}$ and UM-UC-9 LUC lines were injected subcutaneously while the UM-UC-10$^{LUC}$ lines were injected intrabladder in NOD/SCID mice All before, all animals were treated daily for 6 weeks, however 100 μg SL/animal was the dosage rate. The animals were sacrificed after 6 weeks of treatment and wet tumor weights were evaluated to examine the effect of SL on tumor growth. As evident in FIG. 12, there was a significant reduction in tumor size for all three cell lines when compared to the untreated mice. The confidence level for the differences was at least 95% for all three cell lines. These results indicate that SLs are potential pharmaceutical compounds for cancer treatment.

Figure 13:
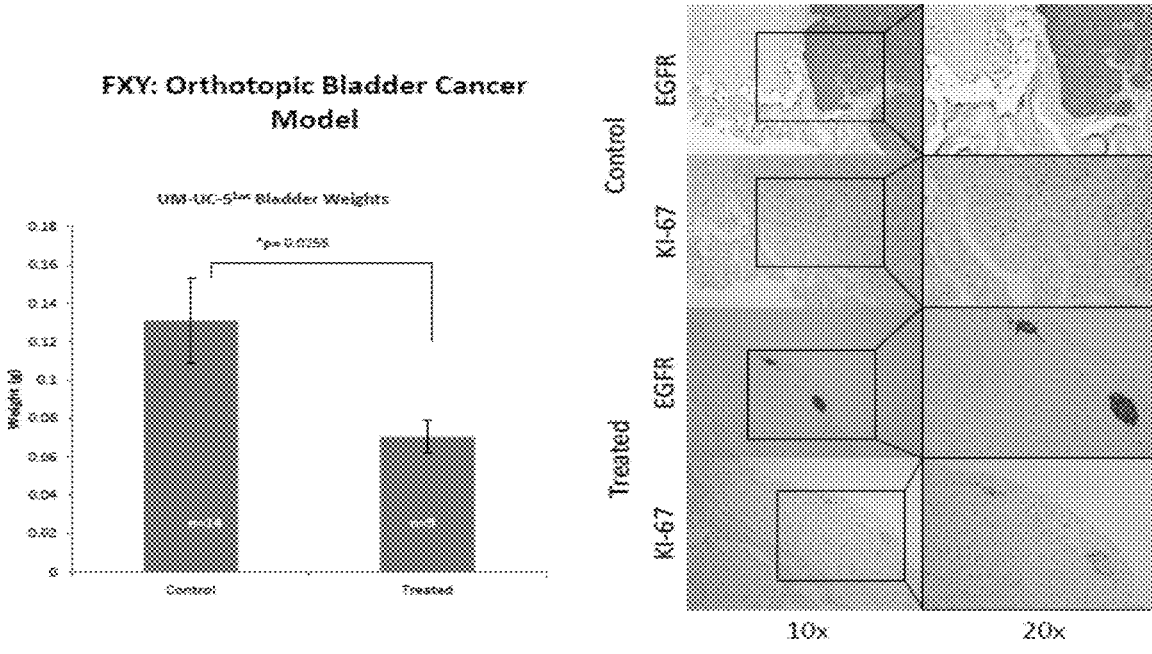
FIG. 13 displays the histopathology of $UM-UC-5^{LUC}$ bladder cell line orthotopically injected into animals and the bladder weights for both control mice and mice treated with the organic extraction of sesquiterpene lactones extracted from *Ambrosia maritima* at a dose of 200 μg/day.
Figure 14:
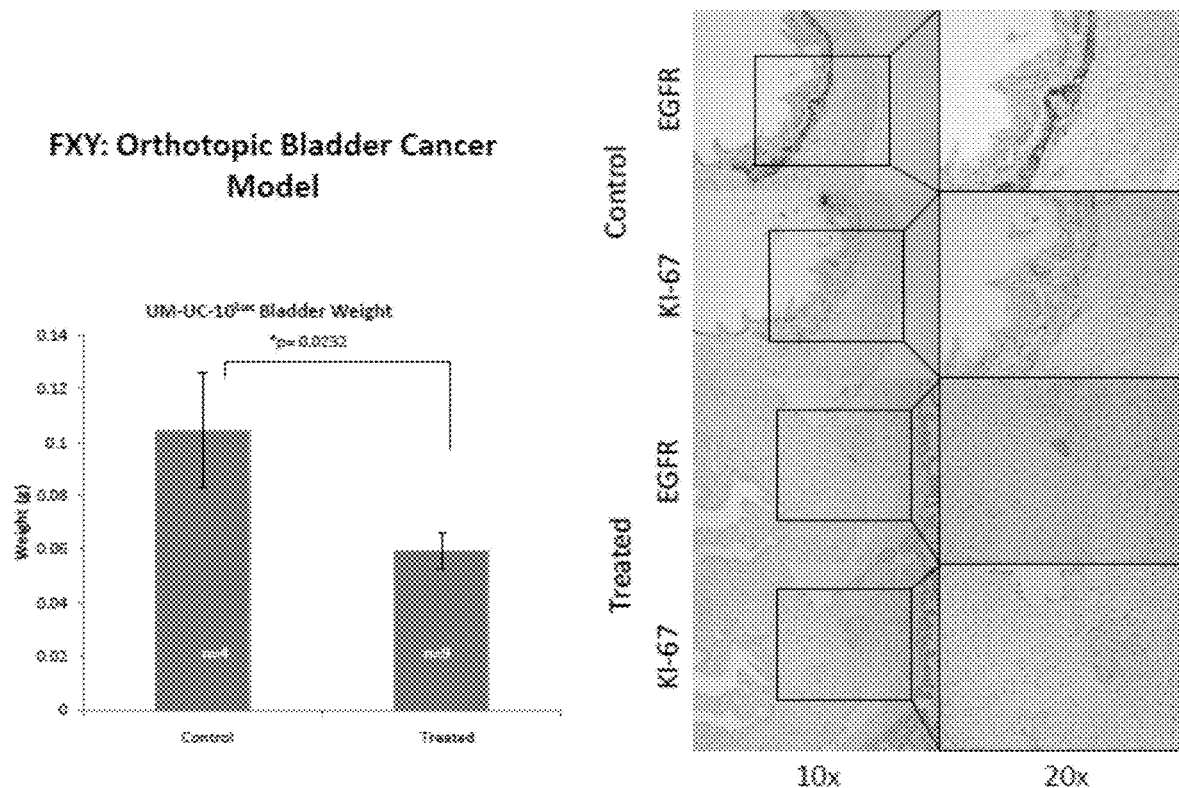
FIG. 14 displays the histopathology of $UM-UC-10^{LUC}$ bladder cell line orthotopically injected into animals and bladder weights for both control mice and mice treated with the organic extraction of sesquiterpene lactones extracted from *Ambrosia maritima* at a dose of 200 μg/day.

FIG. 13 illustrates the histopathology of UM-UC-5$^{LUC}$ orthotopically injected into animals treated with the organic extraction at a dose of 200 μg of SLs/day. In the control animal EGFR and Ki-67 (anti Human) stained the tumor on the other hand there were reduced tumor in the treated animal. The same results were found in the UM-UC-10$^{LUC}$ orthotopically injected animal FIG. 14.

Similar results were obtained with prostate cancer and triple negative breast cancer cell lines.

SPHERE FORMATION

In addition to the in vitro and in vivo experiments, the ability to prevent sphere formation using SLs was also tested.

Sphere-forming assays have been widely used to retrospectively identify stem cells based on their reported capacity to evaluate self-renewal and differentiation at the single cell level in vitro. We study the effects of SL on cancer progenitors (stem cells), sphere-forming assays were performed on cells after treatment with SLs.

Figure 15:
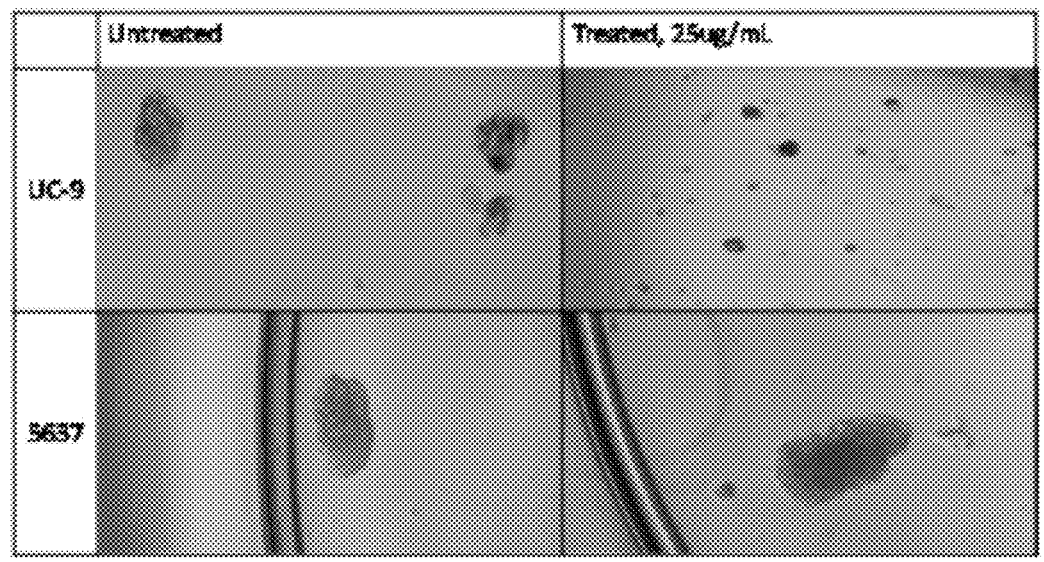
FIG. 15 displays images of spheres form from different bladder cell lines that have been treated (right column) with sesquiterpene lactones or left untreated (left column).

FIG. 15 shows the images of the cell spheres for UM-UC-9 and 5637 bladder cell lines that have been treated with 25 μg/mL SLs and untreated. At this concentration, there was a reduction of sphere formation of the UM-UC-9 cell line. Thus, as expected, UM-UC-9 showed less sphere formation than the 5637 cell lines.

Figure 16:
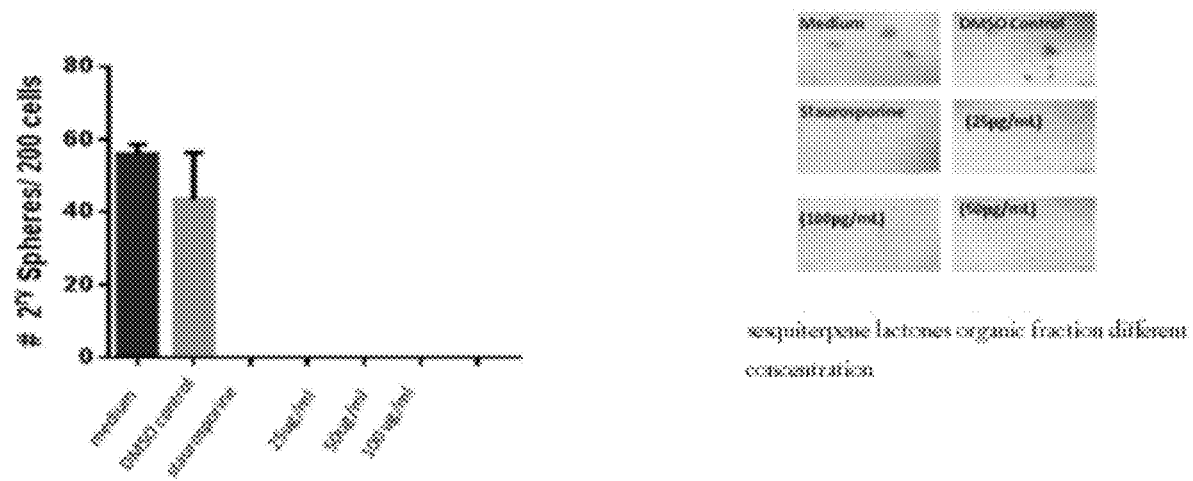
FIG. 16 displays a Sphere Formation Assay for secondary spheres formed from UM-UC-9 and treated with sesquiterpene lactones.

The UM-UC-9 cells were also plated in low adherence plates with a Mammocult medium (Stem Cell Technologies, Inc.) and incubated for 7 days for primary sphere formation. Then, the primary formed spheres were collected and disrupted then plated in a low adherence, 96 well plate with approximately 200 cells/well. The next day, the cells were treated with various concentrations of SLs and the secondary (2ry) sphere formation was analyzed after 7 days. The secondary spheres are representative of the tumor progenitors population. As shown in FIG. 16, the SLs, in concentrations of 25, 50 and 100 μg/mL, greatly reduced the secondary sphere formation as compared to the DMSO control treatment. For each concentration of SLs, total inhibition of the secondary spheres was seen.

Figure 17:
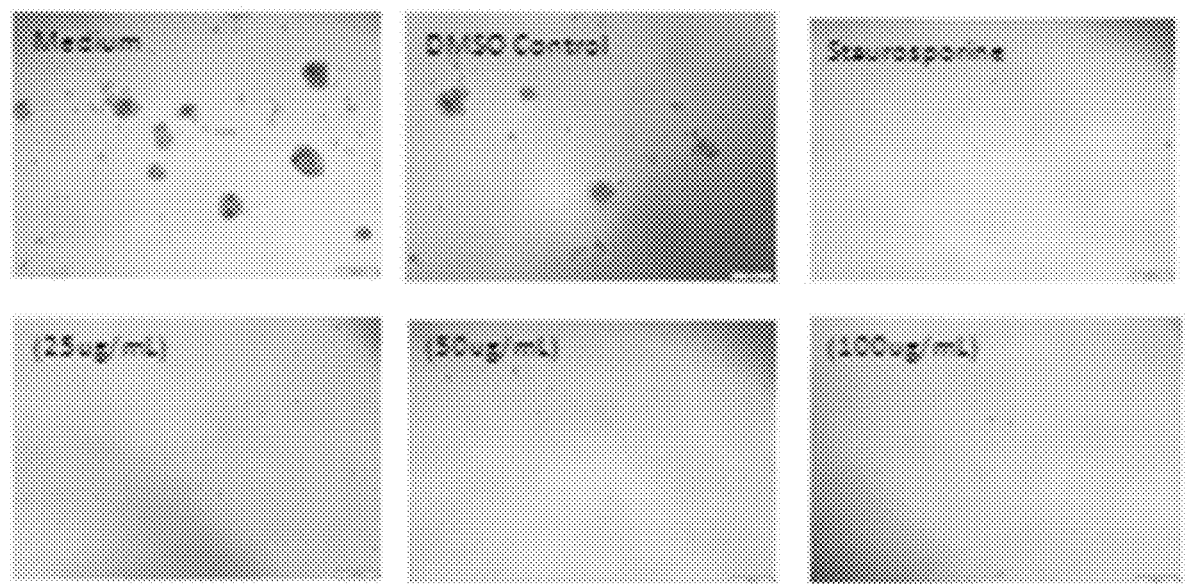
FIG. 17 displays a Sphere Formation Assay for tertiary spheres formed from UM-UC-9 and treated with sesquiterpene lactones.

Tertiary sphere formation was also tested and the results are shown in FIG. 17. Again, sphere formation was inhibited. The β-catenin pathway is also a potential target for the tumor sphere inhibition by SLs.

Ability to reduce or inhibit sphere formation is further evidence of SL's pharmacological advantages in cancer treatment.

IN VITRO DOSE-RESPONSE STUDIES

MTS was used to evaluate $IC_{50}$ (drug concentration causing 50% inhibition of the desired activity) for SLs on various bladder, prostate, breast, lung and pancreatic cancer cell lines.

Figure 18:
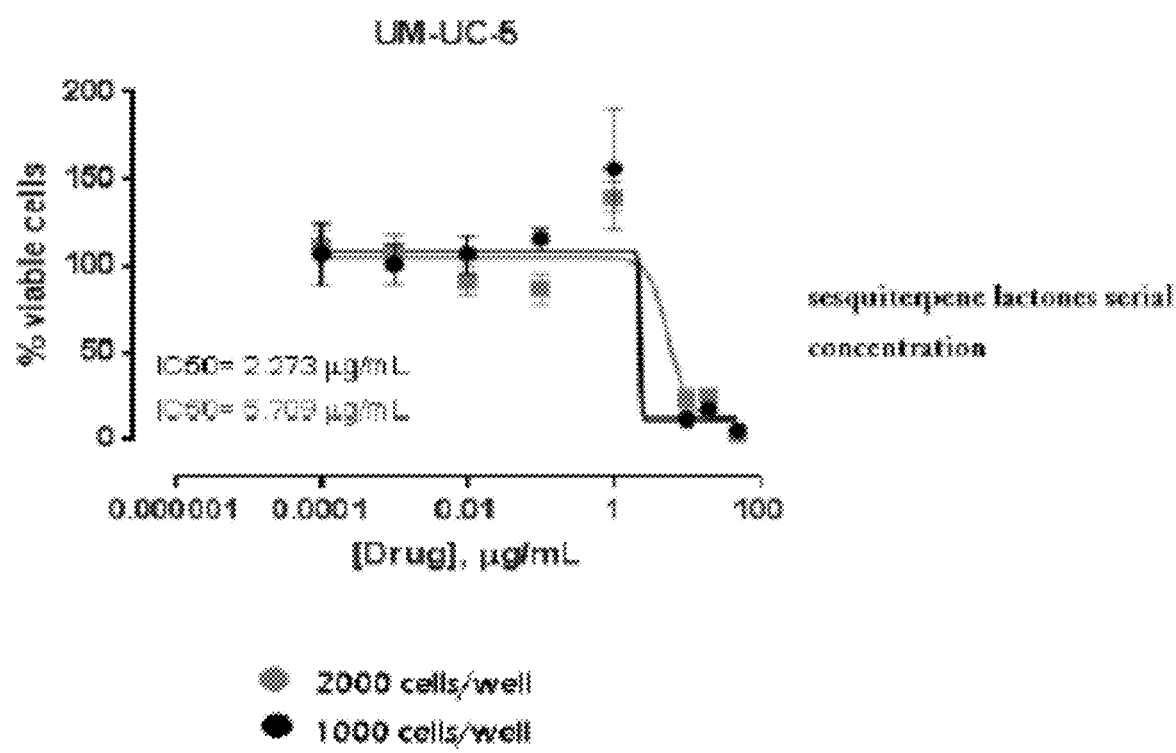
FIG. 18 displays results of $IC_{50}$ experiments on UM-UC-5 bladder cancer cell lines treated with the sesquiterpene lactones found in the organic extract of *Ambrosia maritima*.
Figure 19A:
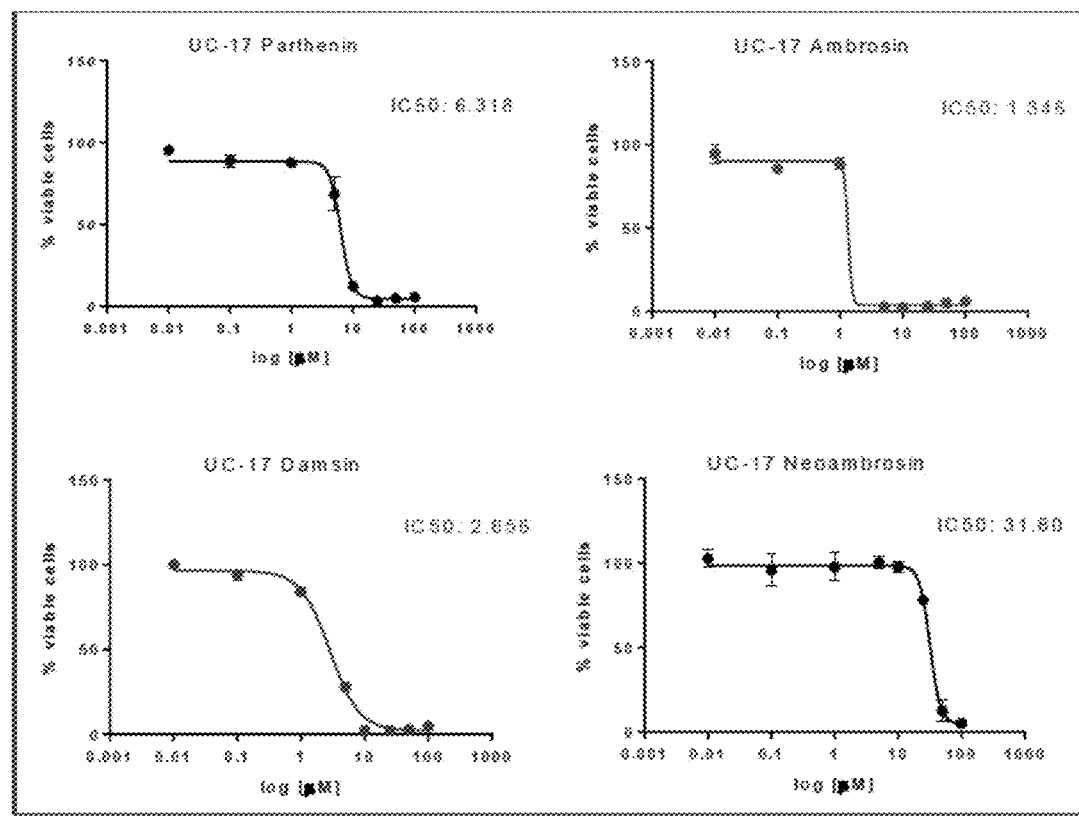
FIG. 19A-D displays results of $IC_{50}$ experiments on bladder cancer cell lines treated with specific sesquiterpene lactones purified from the organic extracted of *Ambrosia maritima*. The purified sesquiterpene lactones are Parthenin, Ambrosin, Damsin, and Neoambrosin. The bladder cancer cell lines are UM-UC-17 (FIG. 19A), UM-UC-9 (FIG. 19B), UM-UC-15 (FIG. 19C), and UM-UC-7 (FIG. 19D).
Figure 19B:
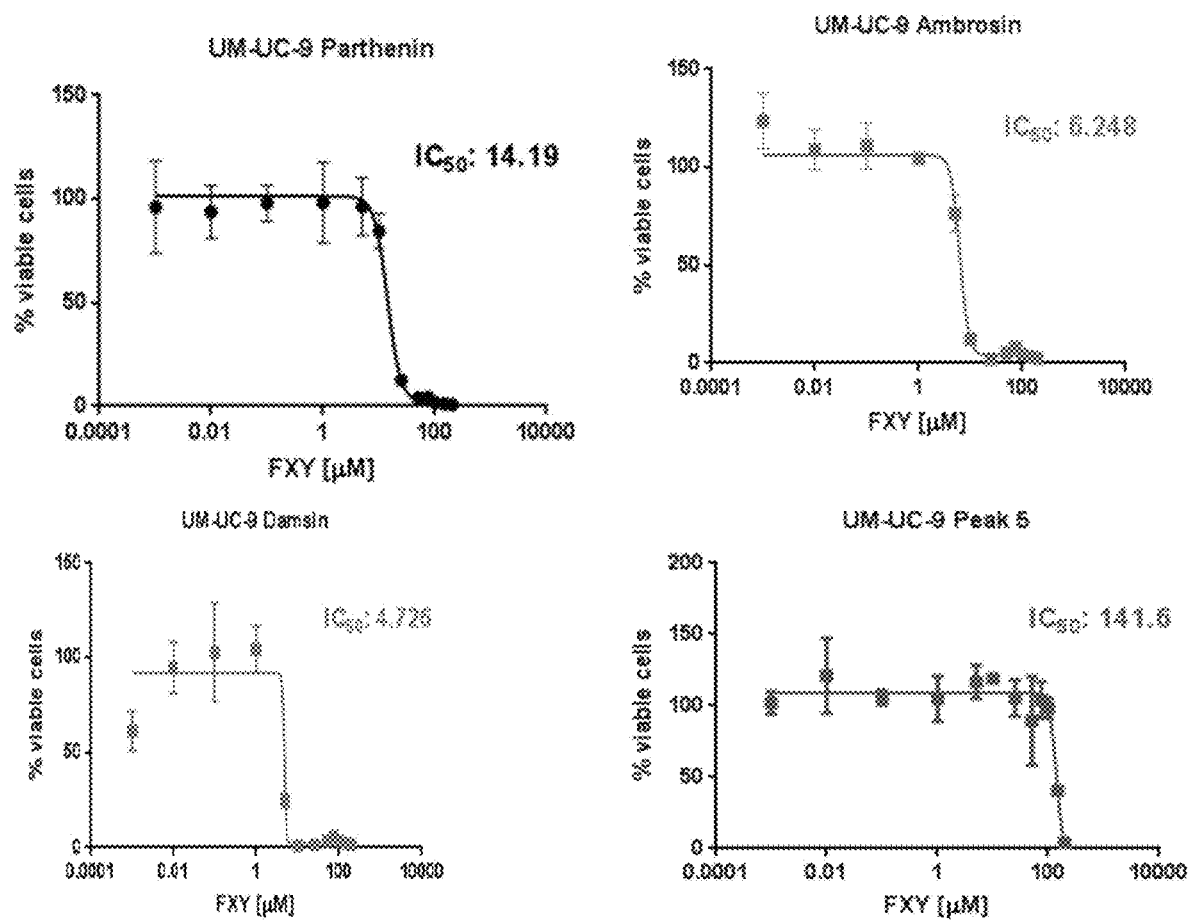
Figure 19C:
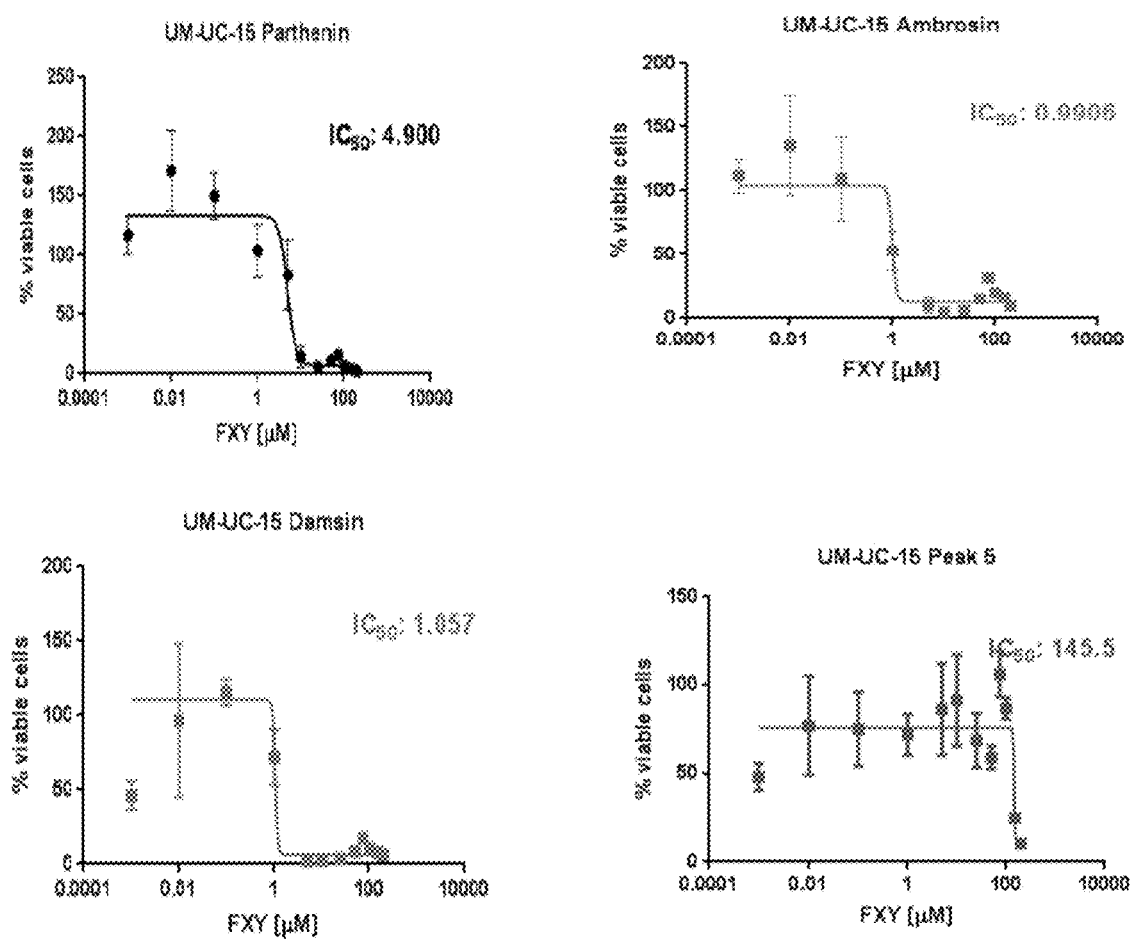
Figure 19D:
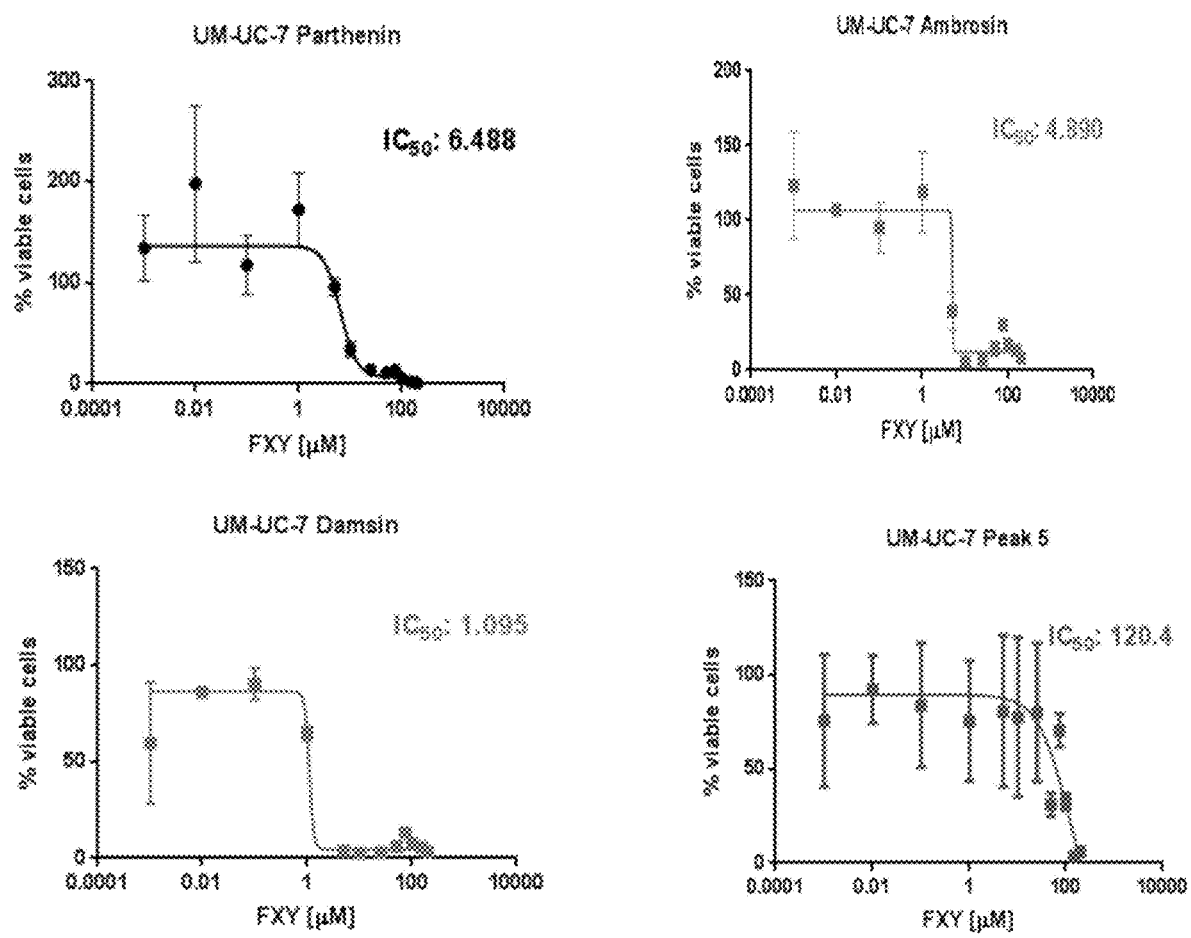

Bladder Cancer Cell Line: The bladder cancer cell line UM-UC-5 was tested with *Ambrosia maritima* extracts. Cells were plated in a 96 well plate at a density of 1000 cells/well and 2000 cells/well. As shown in FIG. 18, the $IC_{50}$ for the 1000 cells/well was 2.273 μg/mL and the $IC_{50}$ for the 2000 cells/well was 5.709 μg/mL.

The MTS test was then conducted to evaluate the different $IC_{50}$ of multiple cell lines. Purification was performed to separate the organic extract of SLs into different components. Micromolar doses, instead of micrograms, as determined by the molecular weight of the different SLs, Parthenin, Ambrosin, Damsin, and Neoambrosin, were tested in vitro. Ideally, for drug treatments, micromolar weights between 10-15 are preferred. Each cell line was plated at a density of 1000 cells/well and the $IC_{50}$ results are shown in FIG. 19A-D and Table 2.

TABLE 2

$IC_{50}$ results (in μM) for bladder cancer cell lines and individual SLs

|  | PARTHENIN | AMBROSIN | DAMSIN | NEOAMBROSIN |
| --- | --- | --- | --- | --- |
| UM-UC-17 | 6.318 | 1.346 | 2.856 | 31.80 |
| UM-UC-9 | 14.19 | 6.248 | 4.726 | 141.6 |
| UM-UC-15 | 4.9 | 0.9906 | 1.057 | 145.5 |
| UM-UC-7 | 6.488 | 4.89 | 1.095 | 120.4 |

As expected from our other experiments, ambrosin and damsin had the best $IC_{50}$ results. Even from UM-UC-9, which is a muscle invasive bladder cancer, the $IC_{50}$ was well below the 10 μM target range for drug treatments.

Though neoambrosin showed the least efficacy of these four SLs, it can still find use in treatments using the whole extraction or in combination with other SLs.

In review of the results between the SLs that were tested for their $IC_{50}$, it can be concluded that different bladder cancer cell lines responded differentially to different SLs. Thus, there are different degrees of sensitivity of the different cell lines tested for bladder cancer.

Figure 20A:
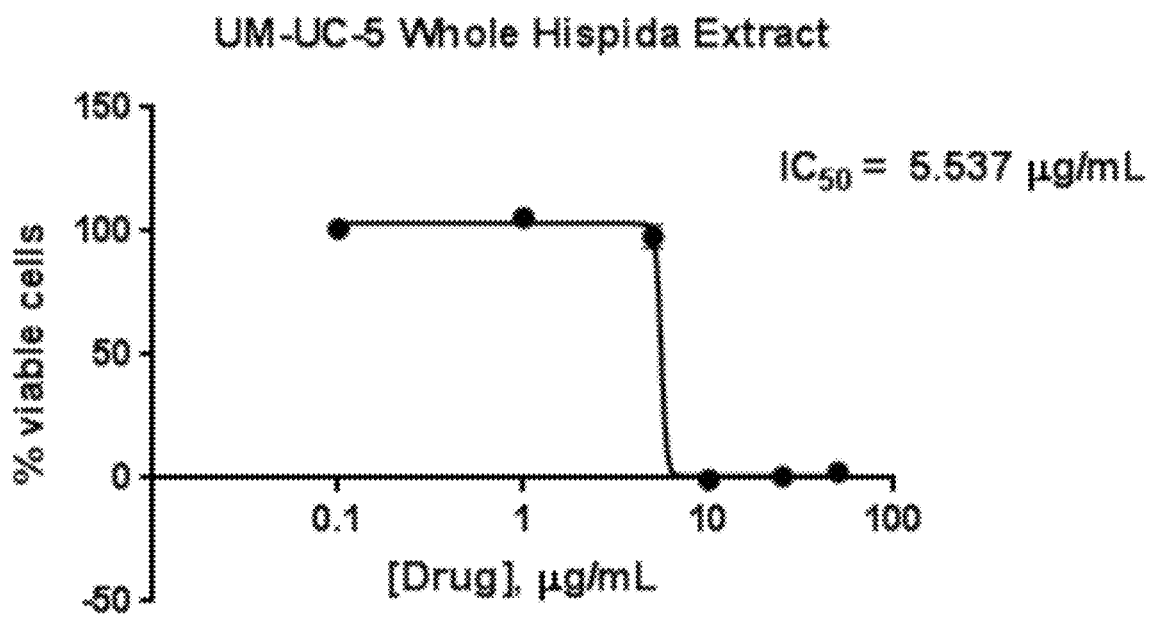
FIG. 20A displays results of $IC_{50}$ experiments on UM-UC-5 bladder cancer cell lines treated with the sesquiterpene lactones found in the organic extract of *Ambrosia hispida*.
Figure 20B:
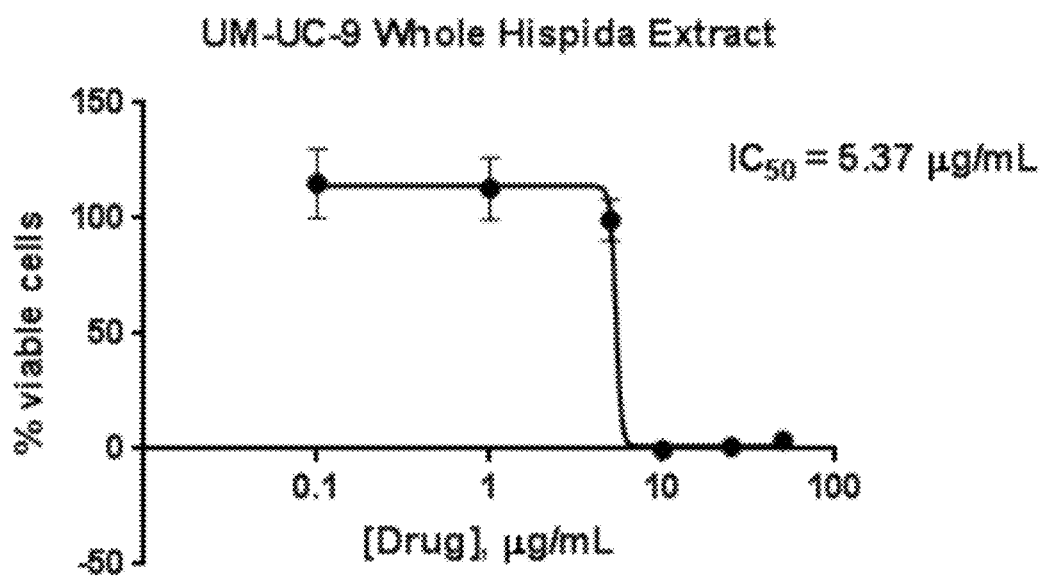
FIG. 20B displays results of $IC_{50}$ experiments on UM-UC-9 bladder cancer cell lines treated with the sesquiterpene lactones found in the organic extract of *Ambrosia hispida*.
Figure 20C:
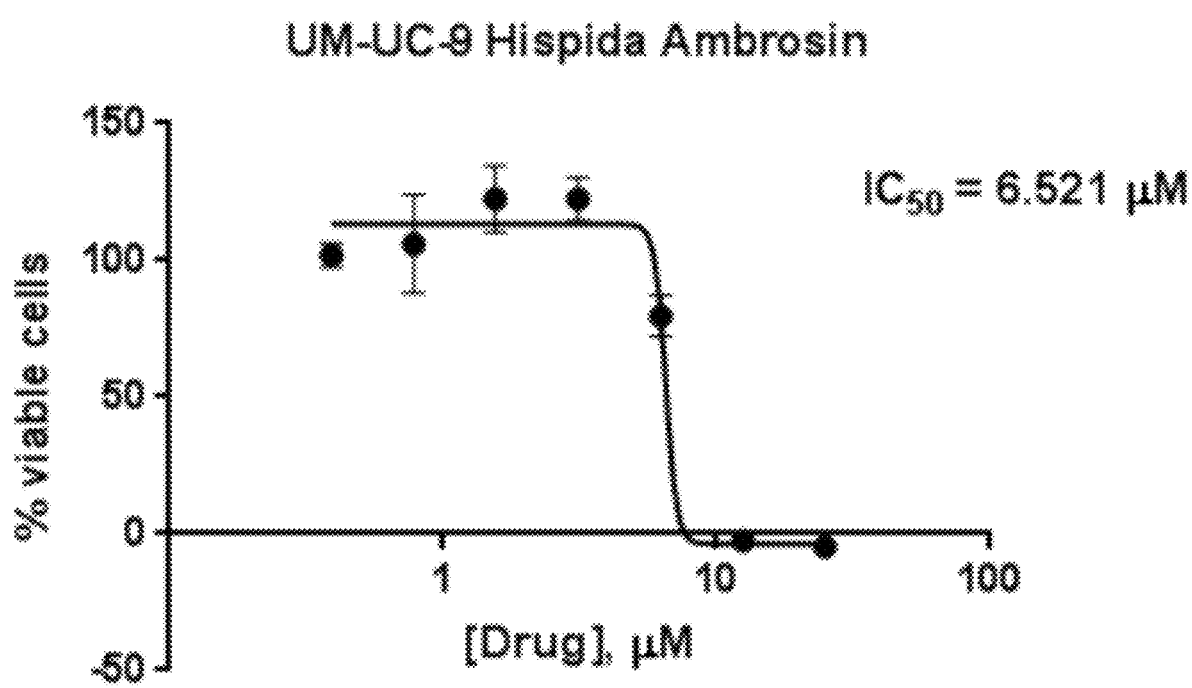
FIG. 20C displays the results of $IC_{50}$ experiments on bladder cancer cell lines treated with purified Ambrosin from the organic extracted of *Ambrosia hispida*.

Similar tests were performed with the organic extract from *Ambrosia hispida*. FIG. 20A-C displays results of the $IC_{50}$ test for UM-UC-5 and UM-UC-9 bladder cell lines with the whole extract and with just Ambrosin purified from the organic extract.

Breast Cancer Cell Lines: Tumors that lack expression of estrogen receptor, progesterone receptor and less expression of HER2 are recognized as triple negative breast cancer (TNBC). TNBC tumors are further subdivided into molecular subtypes including the claudin-low tumors that have similar properties to stem cells in addition to features of epithelial-to-mesenchymal transitions. Interferon-rich subtype are tumors with better prognosis than normal breast like subtype.

Figure 21A:
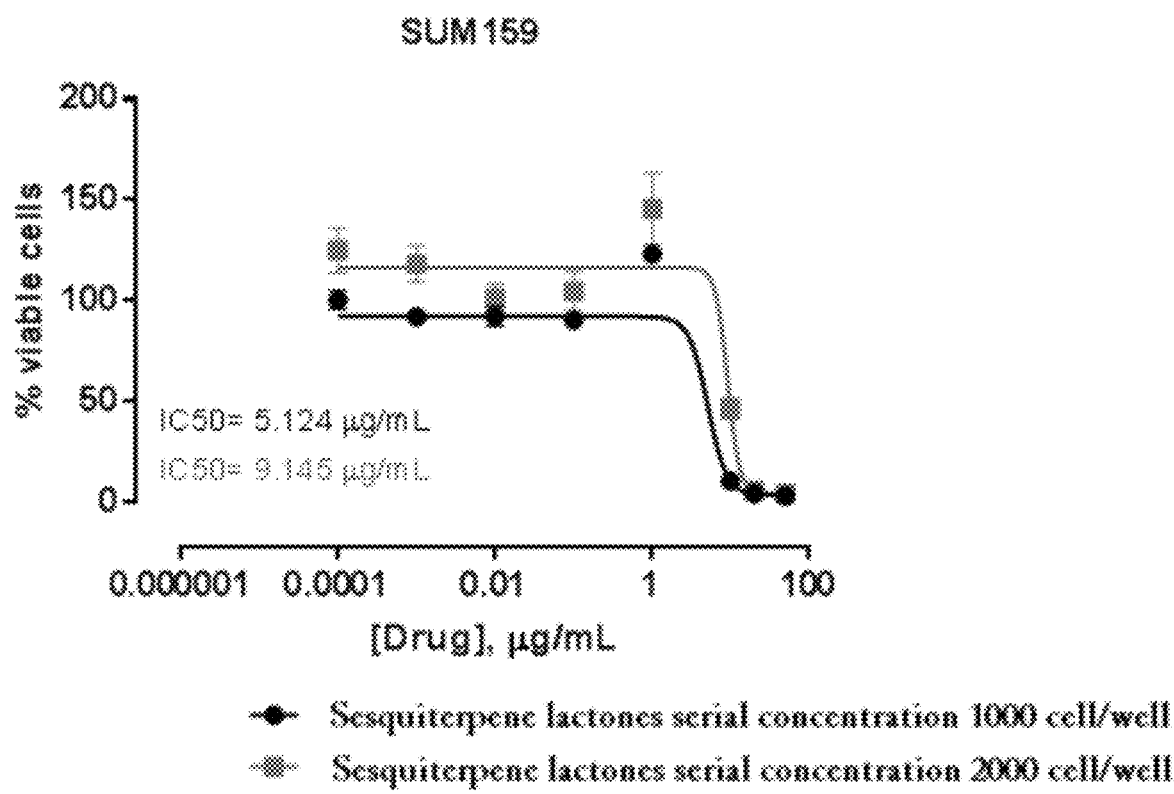
FIG. 21A displays results of $IC_{50}$ experiments on breast cancer cell line SUM159 and FIG. 21B displays results for breast cancer cell line MDA-MB-231 treated with the organic extraction of sesquiterpene lactones extracted from *Ambrosia maritima*.
Figure 21B:
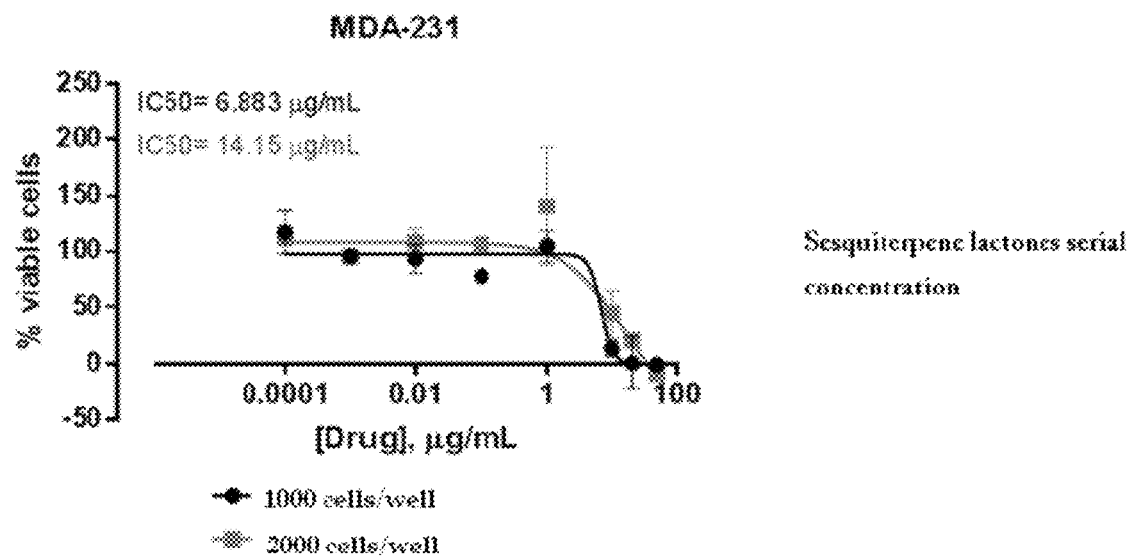

Several TNBC cell lines were tested in vitro and were treated with serial concentrations of the extracted SLs from *Ambrosia maritima* to determine $IC_{50}$. The results of the $IC_{50}$ experiments for the SUM-159 (Basal, Claudin Low) and MDA-MB-231 (Basal, Claudin Low) cell lines are shown in FIG. 21A-B. The SLs showed efficacy in inhibiting triple negative breast cancers at various concentrations of SLs. Results are summarized in Table 3.

TABLE 3

$IC_{50}$ results (in µg/mL) for triple negative breast cancer cell lines treated with SLs extracted from *Ambrosia maritima*

|  | 1000 CELL/WELL | 2000 CELL/WELL |
| --- | --- | --- |
| SUM159 | 5.124 | 9.145 |
| MDA-231 | 6.883 | 14.15 |

Figure 22:
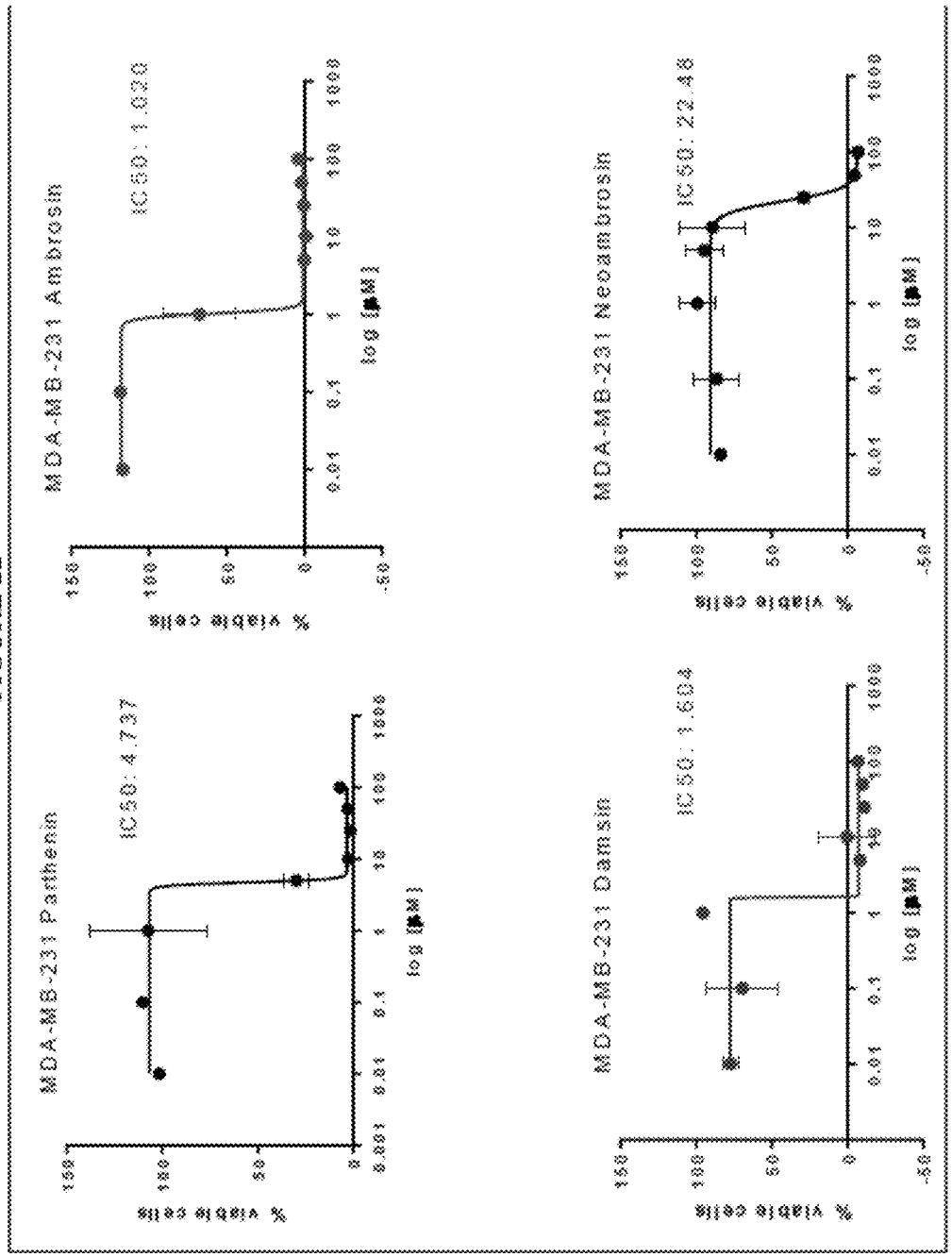
FIG. 22 displays results of $IC_{50}$ experiments on breast cancer cell line MDA-MB-231 treated with specific sesquiterpene lactones purified from the organic extracted of *Ambrosia maritima*. The purified sesquiterpene lactones are Parthenin, Ambrosin, Damsin, and Neoambrosin.
Figure 23:
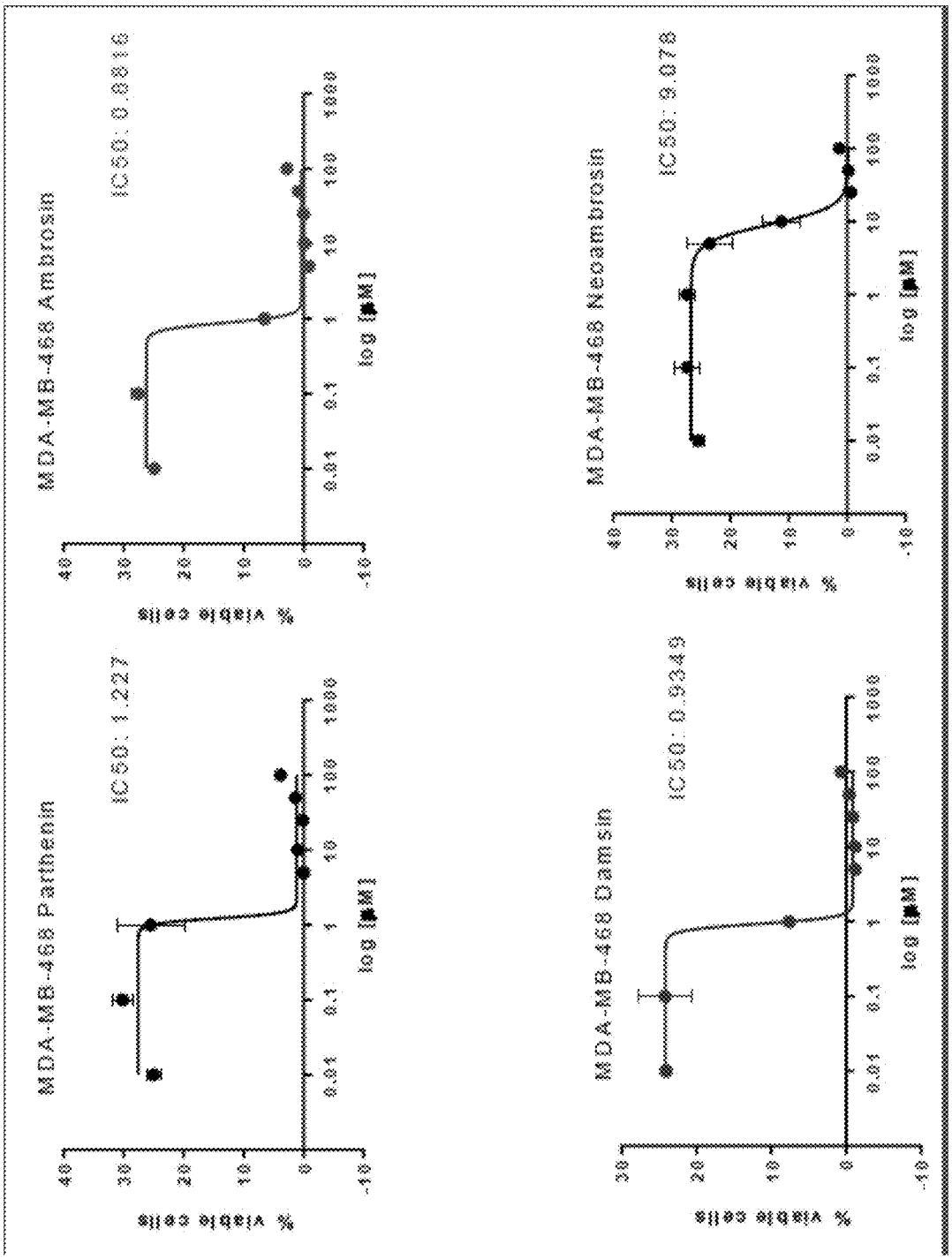
FIG. 23 displays results of $IC_{50}$ experiments on breast cancer cell line MDA-MB-468 treated with specific sesquiterpene lactones purified from the organic extracted of *Ambrosia maritima*. The purified sesquiterpene lactones are Parthenin, Ambrosin, Damsin, and Neoambrosin.
Figure 24:
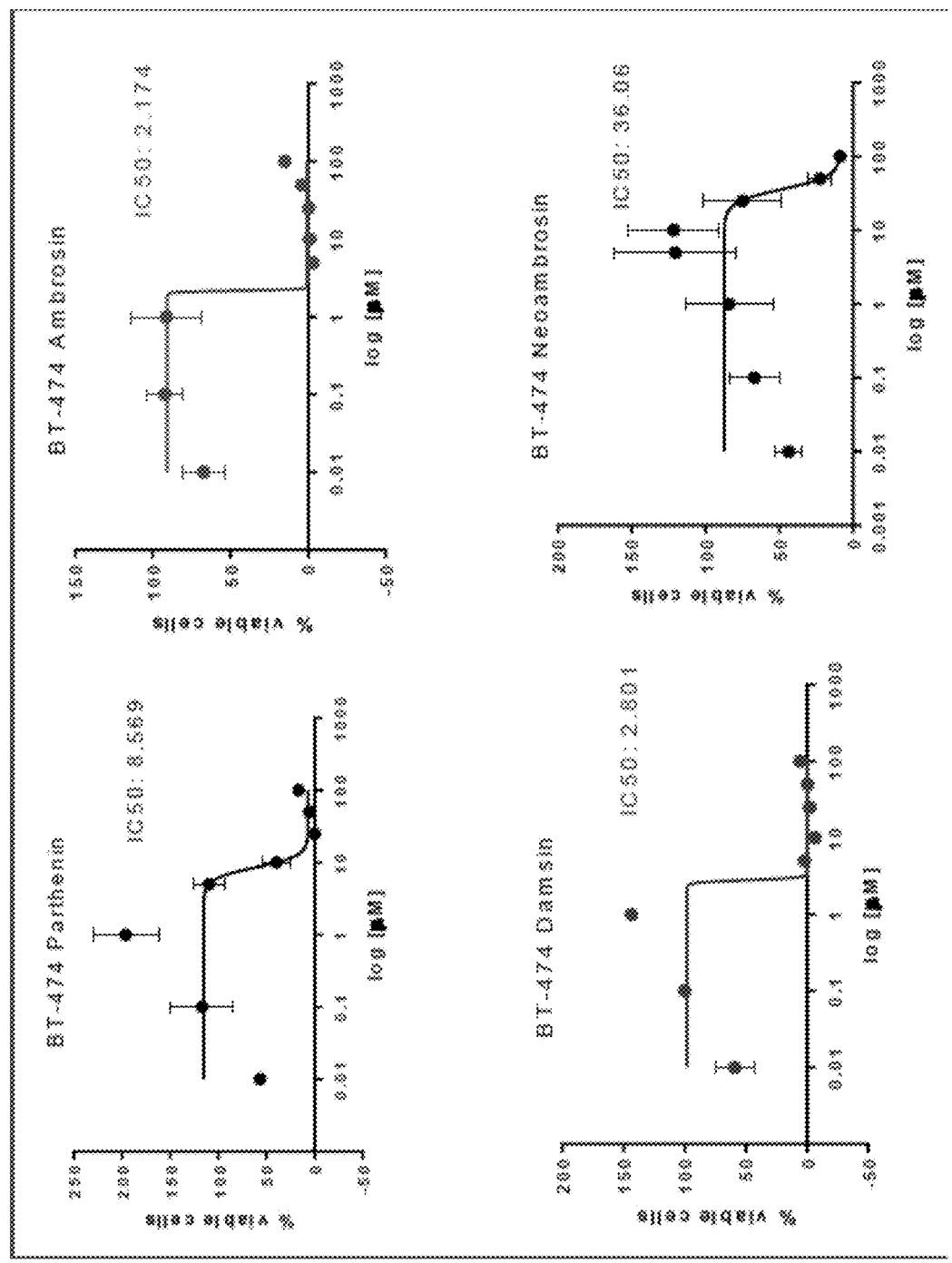
FIG. 24 displays results of $IC_{50}$ experiments on breast cancer cell line BT-474 treated with specific sesquiterpene lactones purified from the organic extracted of *Ambrosia maritima*. The purified sesquiterpene lactones are Parthenin, Ambrosin, Damsin, and Neoambrosin.

The $IC_{50}$ of the purified SLs, Parthenin, Ambrosin, Damsin, and Neoambrosin, were also tested for MDA-MB-231 cell line (FIG. 22), MDA-MB-468 (Basal Subtype Normal) cell line (FIG. 23), and BT-474 cell line (FIG. 24), an invasive ductal carcinoma cell line (luminal subtype B). Results are summarized in Table 4.

TABLE 4

$IC_{50}$ results (in µM) for breast cancer cell lines and individual SLs extracted from *Ambrosia maritima*

|  | PARTHENIN | AMBROSIN | DAMSIN | NEOAMBROSIN |
| --- | --- | --- | --- | --- |
| MDA-MB-231 | 4.737 | 1.020 | 1.604 | 22.48 |
| MDA-MB-468 | 1.227 | 0.8816 | 0.9349 | 9.078 |
| BT-474 | 8.569 | 2.174 | 2.801 | 36.06 |

Like the results from the bladder cell tests, the cell lines were sensitive to different SLs. The most sensitive was seen with Neoambrosin, but Parthenin was also effective for BT-474.

Figure 25A:
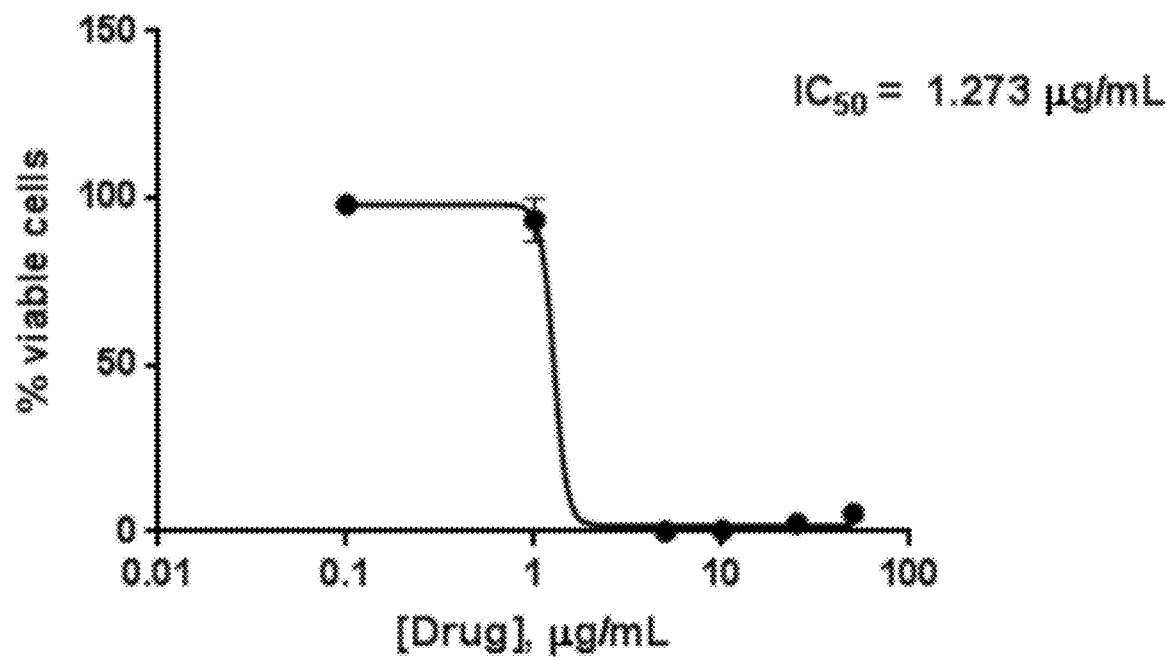
FIG. 25A-B displays results of $IC_{50}$ experiments on breast cancer cell line MDA-MB-231 (25A) and BT-20 (25B) treated with sesquiterpene lactones found in the organic extract of *Ambrosia hispida*.
Figure 25B:
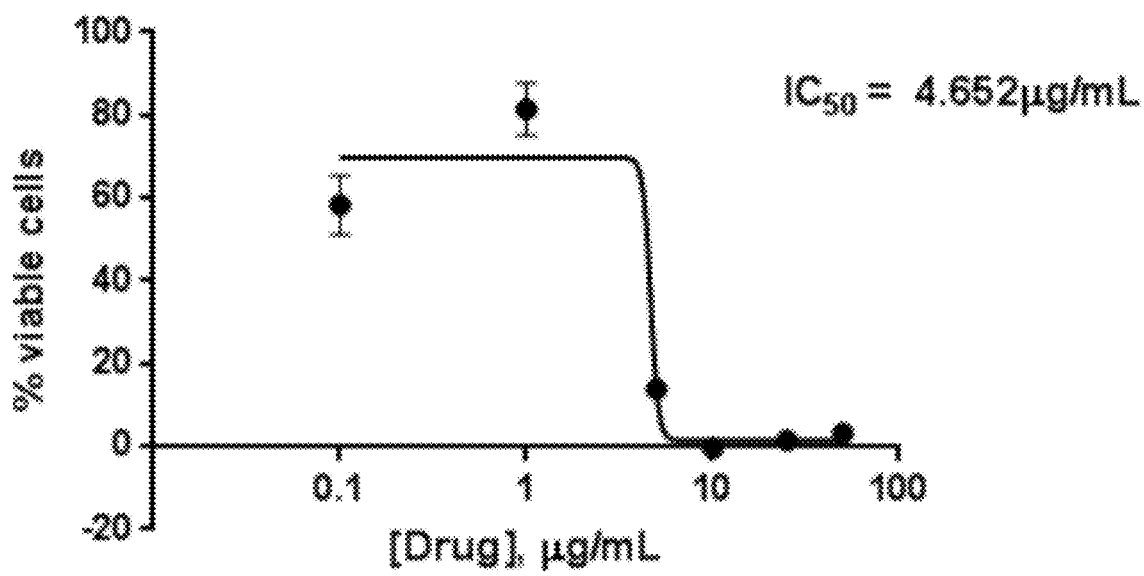
Figure 25C:
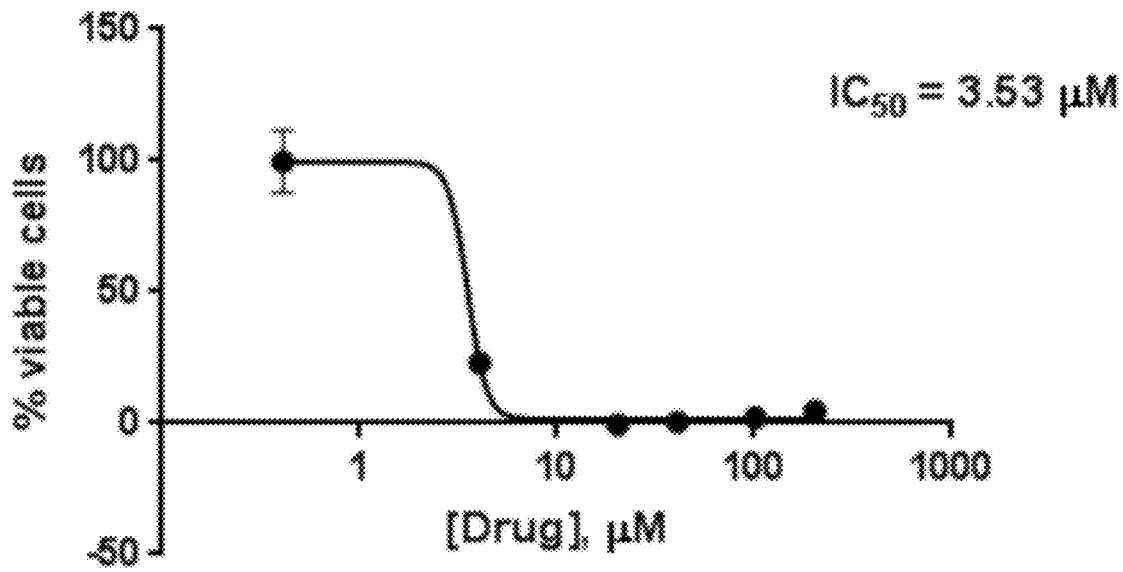
FIG. 25C-D displays the results of $IC_{50}$ experiments on breast cancer cell line MDA-MB-231 (25C) and BT-20 (25D) treated with Ambrosin purified from the organic extract of *Ambrosia hispida*.
Figure 25D:
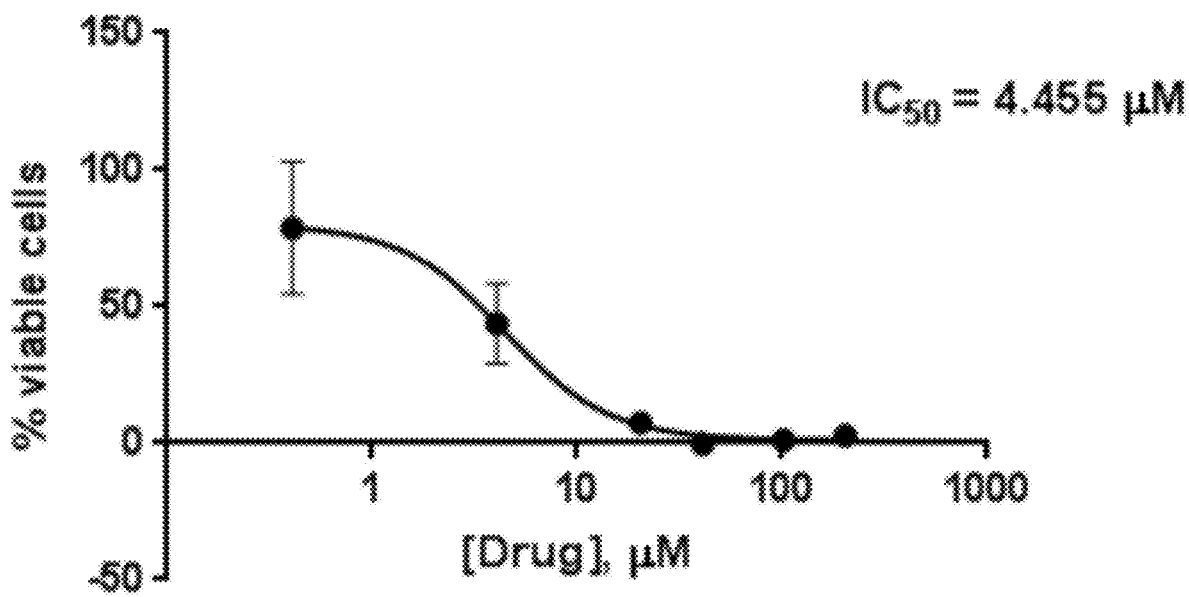

Similar tests were performed with the organic extract from *Ambrosia hispida*. FIG. 25A-B displays results of $IC_{50}$ experiments on breast cancer cell line MDA-MB-231 (25A) and BT-20 (25B) treated with sesquiterpene lactones found in the organic extract of *Ambrosia hispida*. FIG. 25C-D displays the results of $IC_{50}$ experiments on breast cancer cell line MDA-MB-231 and BT-20 treated with Ambrosin purified from the organic extract of *Ambrosia hispida.*

As expected, the different cell lines had different sensitivities to the SLs extracts. Unexpectedly, both breast cancer cell lines had a greater $IC_{50}$ from purified Ambrosin. This may be due to different molecular activity in different cell lines.

Figure 26A:
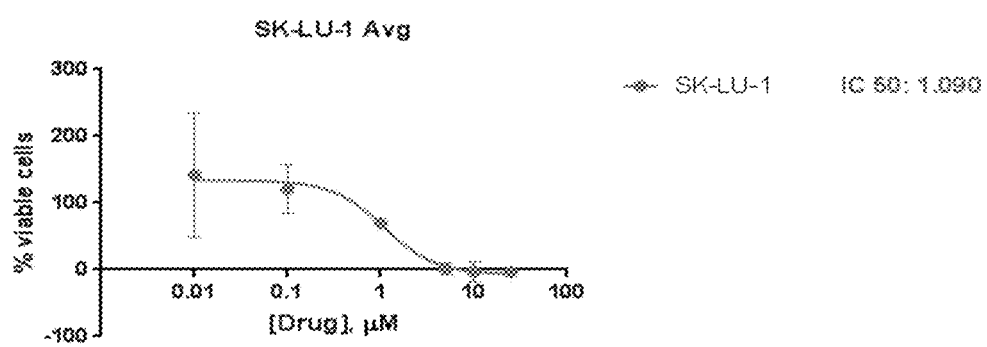
FIG. 26A-B display efficacy and $IC_{50}$ experiments performed on lung cancer cell lines SK-LU-1 (FIG. 26A) and A549 (FIG. 26B).
Figure 26B:
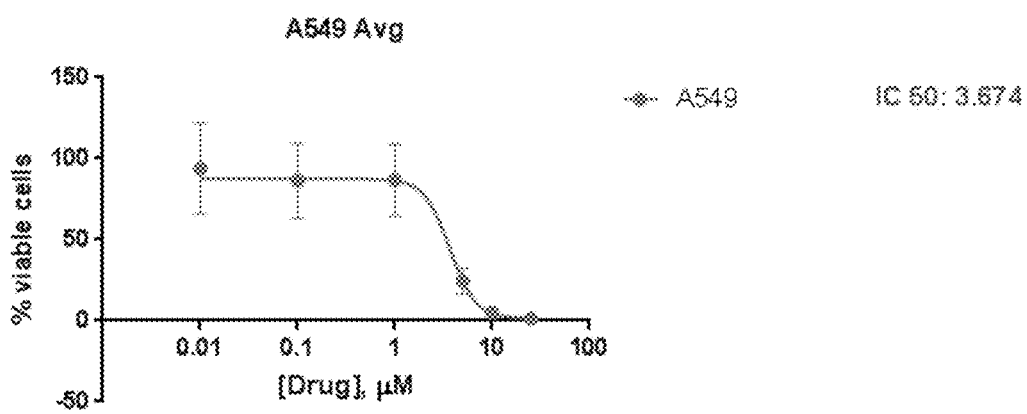

Lung Cancer Cell Lines: Efficacy and $IC_{50}$ experiments were also performed on lung cancer cell lines. SK-LU-1 is an adenocarcinoma cell line of the lung and A549 is a long lung carcinoma cell line. These cell lines were treated with the different sesquiterpene lactones and the average of the three treatments efficacy are shown in FIGS. 26A-B. The $IC_{50}$ is calculated in micromolar.

Figure 27:
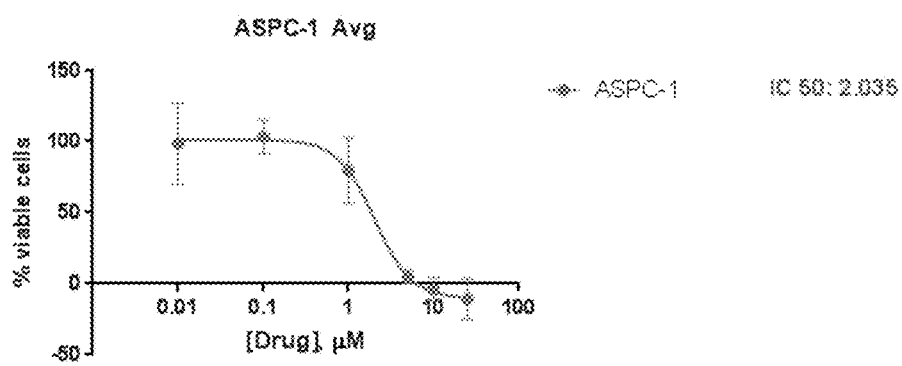
FIG. 27 display efficacy and $IC_{50}$ experiments performed on pancreatic cancer cell lines ASPC-1.

Pancreatic Cancer Cell line: One Pancreatic cell line (ascites metastasis) AsPC-1 was treated with different SLs in a micromolar concentration. The resulted $IC_{50}$ as shown in FIG. 27.

Figure 28A:
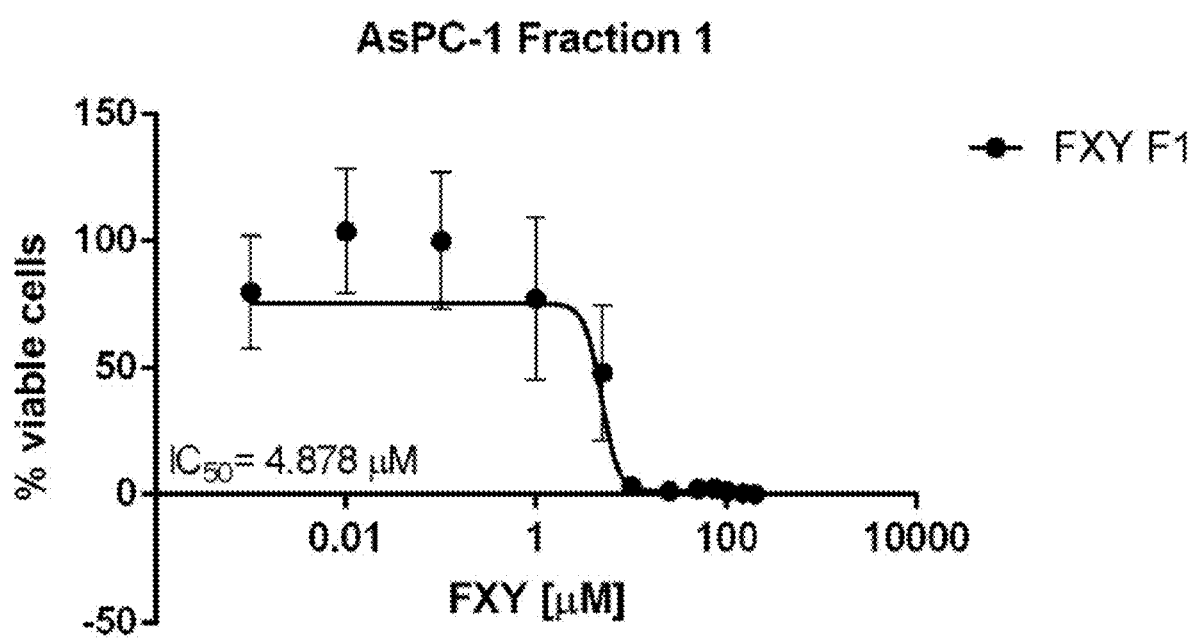
FIG. 28A-D displays results $IC_{50}$ experiments on prostate cancer cell line for different purified sub fractions (1=Parthenin, 3=Ambrosin, 4=Damsin, 5=Neoambrosin) of the organic extraction wherein the $IC_{50}$ is 4.878 (28A), 2.715 (28B), 1.160 (28C) and 264.5 (28D). The concentration is in μmol.
Figure 28B:
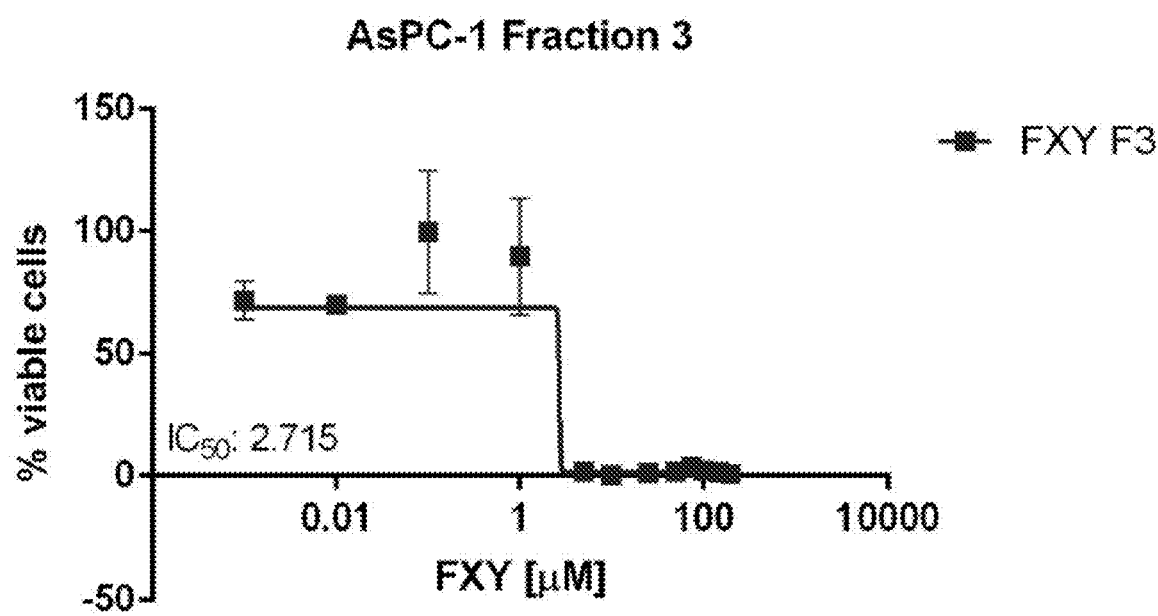
Figure 28C:
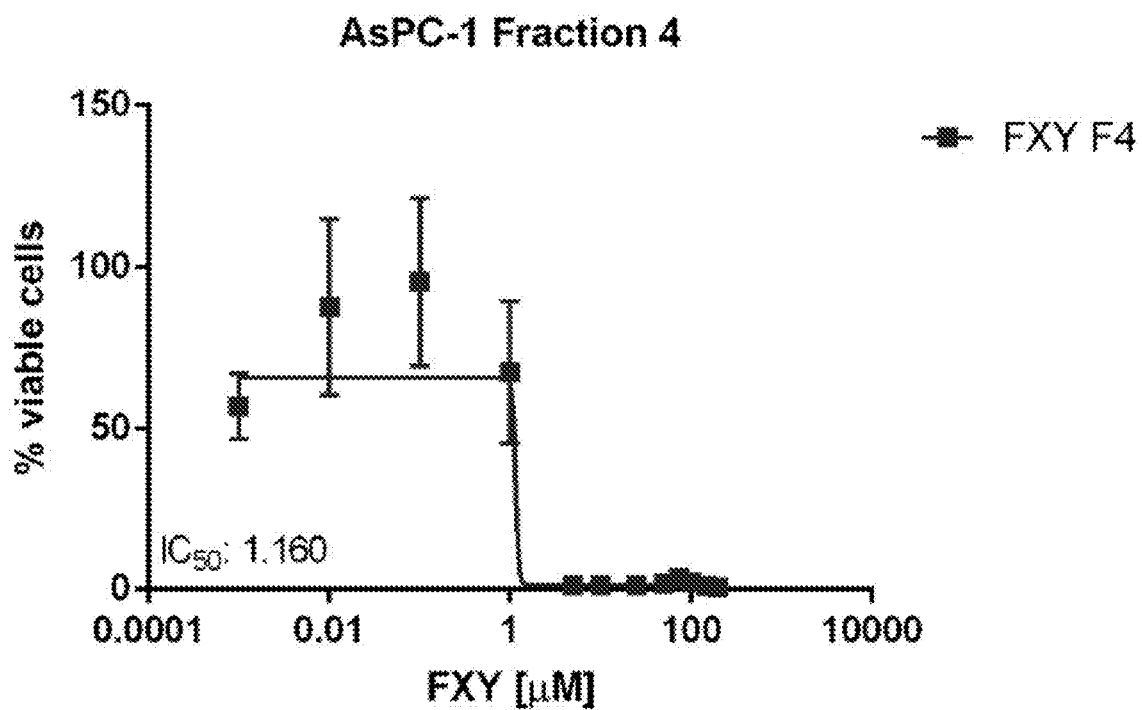
Figure 28D:
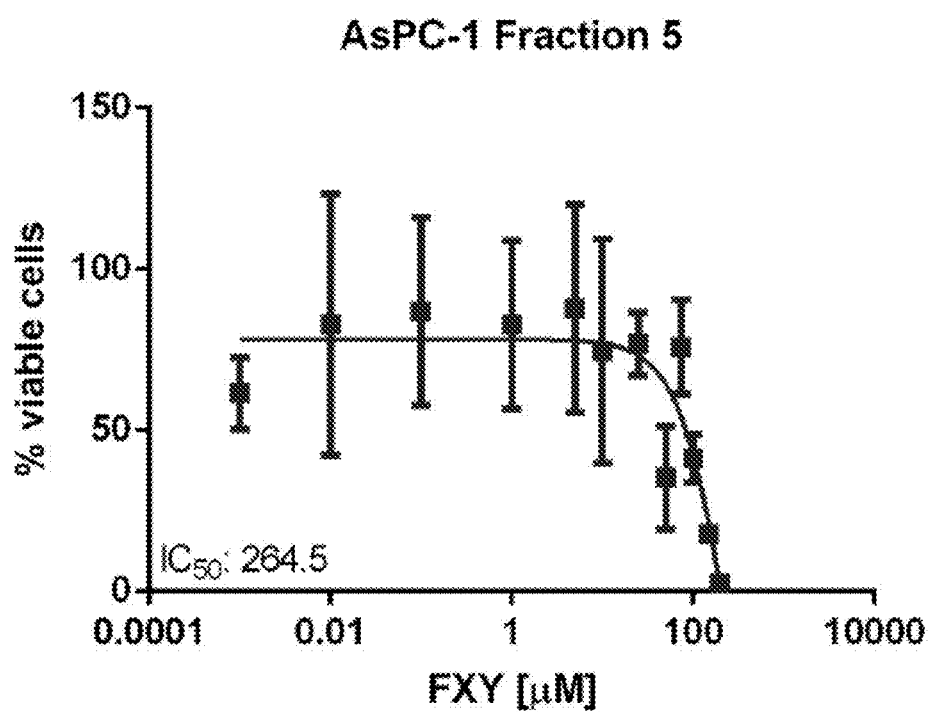

FIG. 28A-D displays results $IC_{50}$ experiments on prostate cancer cell line for different purified sub fractions (1=Parthenin, 3=Ambrosin, 4=Damsin, 5=Neoambrosin) of the organic extraction wherein the $IC_{50}$ is 4.878 (FIG. 28A), 2.715 (FIG. 28B), 1.160 (FIG. 28C) and 264.5 (FIG. 28D). The concentration is in µmol. As expected, some of the sub fractions affected the cell line to a much greater extent to others.

BROMOURIDINE SEQUENCING EXPERIMENT

The steady-state level of a particular RNA in a cell is a balance between its rates of production and degradation. Knowing the relative contribution of RNA synthesis and degradation to the steady-state level of particular transcripts is critical in order to better understand the mechanisms of regulation of these transcripts. Thus, when the cell homeostasis is changed by environmental stimuli or stress, the steady-state levels of some RNA will be altered. This change can then be used to determining whether the ensuing gene expression was the result of the altered RNA synthesis, stability or both.

As such, the RNA of cancer cells can be sequenced and compared to normal cells to see where there is more or less (i.e. altered) RNA. That can help lead to the gene or protein that might be triggering the cancer.

A common method of monitoring RNA changes is by labeling new RNA with Bromouridine, then isolate the RNA to see where the new RNA was made. Bromouridine sequencing is well known in the art.

We used this method to monitor RNA in the UM-UC-9 (bladder) and BT-20 (breast) cancer cell line to detect the level of nascent transcription on the genome after treatment with SLs. Both cell lines were treated with the whole organic fraction at one time, or purified Ambrosin from the organic fraction at different doses for 3.5 hours. The RNA was then labeled with Bromouridine for half an hour and sequenced to detect the level of nascent transcription in the genome.

The hallmark targets that were affected in their transcription upon treatment were then reviewed. Some of the hallmarks are directly related to cancer progression and proliferation that the treatment whether with the organic fraction or the purified Ambrosin caused the genes to be deregulated by transcribing them at lower level than the control.

Upon treatment with the organic fraction or with the purified Ambrosin at different doses, genes that affected the apoptotic pathway, reactive oxygen species pathway, among others vital to cancer progression, were upregulated. Thus, the SLs and Ambrosin are able to reduce, if not stop, some of these pathways and slow or reduce the cancer progression.

The present invention is exemplified with respect to the examples and description using extracts from the *martima* and *hispida* plants. However, this is exemplary only, and the invention can be broadly applied to any *Ambrosia* plant. Further, any SLs found in these plants are expected to show some level of cytotoxicity for cancer treatment. The foregoing examples are intended to be illustrative only, and not unduly limit the scope of the appended claims.

The following references are incorporated by reference in their entirety.

Tackholm, Vivi. (1974). Student's flora of Egypt. 2nd edition, Cairo University, Egypt.

Sherif, A. F. and M. F. El-Savvy, (1977). Field trials of the Molluscicidal action of Ambrosia maritima (Damesisa). Bull. High Inst. Puplic Health Alex. 7:1-4.

El Sawy M F, El Hamd Z M S, Loutfy N F, El Masry S and Abdel Gualil M Z (1986): J of the Egypt. Society of Parasitology, 16:1, pp 57-64.

Abdallah, O. M.; Ali, A. A. and Itokawa, H. (1991). "Cytotoxic activity of Sesquiterpene lactones isolated from Ambrosia maritima". Pharmazie, 46(6):472.

Badawy, M.; Abdelgaleil, S. A. M.; Suganuma, T. and Fuji, M. (2014). "Antibacterial and biochemical activity of Pesudoguaianolide Sesquiterpene isolated from Ambrosia maritima against plant pathogenic bacteria". Plant protect. Sci. 50 (2): 64-69.

Alard, F.; Stievenart, C; Vanparys, L. and Geerts, S. (1991). Drug and Chemical Toxicol. 14(4):353-373.

Basseres, D. S. and Baldwin, A. S. (2006). Nuclear factor-κB Kinase pathways in oncogenic initiation and progression. Oncogene. 25: 6817-6830.

Yue, P. and Turkson, J. (2009). Targeting STAT3 in cancer: how successful are we? Expert Opin Investig Drugs. 18(1): 45-56.

Mackenzie, S. H.; Clay Clark, A. (2012). Death by caspase dimerization. Adv Exp Med Biol.: 747: doi:10.1007/978-1-4614-3229-6_4.

Girgert, R.; Emons, G. and Grundker, C. (2014). Inhibition of GPR30 by estriol prevents growth stimulation of triple-negative breast cancer cells by 17 β-estradiol. BMC cancer. 14:935.

William, D; Foulk, M. B.; Smith, M. D.; Ian E. S. and Jorge S. (2010). N Engl J Med 363: 1938.

The invention claimed is:

1. A method of treating bladder cancer or pancreatic cancer, comprising administering an effective amount of a composition comprising a clean organic extract of Ambrosia maritima together with a pharmaceutically acceptable carrier to a patient with bladder cancer or pancreatic cancer, whereby the clean organic extract of said Ambrosia maritima is prepared by treating a plant of Ambrosia maritima with a polar organic solvent, evaporating the polar organic solvent to produce a crude extract, subjecting the crude extract to chromatography using a second organic solvent to obtain said clean organic extract.

2. The method of claim 1, wherein said effective amount is administered daily for at least 6 weeks.

3. The method of claim 1, wherein said clean organic extract comprises at least one sesquiterpene lactone.

4. The method of claim 1, wherein said clean organic extract comprises one or more of the following sesquiterpene lactone: parthenin, ambrosin, damsin, and neoambrosin.

5. The method of claim 1, wherein said clean organic extract comprises parthenin, ambrosin, damsin, and neoambrosin.

6. A method of treating bladder cancer or pancreatic cancer, comprising administering an effective amount of a composition comprising sesquiterpene lactones extracted from Ambrosia hispida together with a pharmaceutically acceptable carrier to a patient with bladder cancer or pancreatic cancer, whereby said sesquiterpene lactones are prepared by treating Ambrosia hispida with a polar organic solvent, evaporating the polar organic solvent to produce a crude extract, subjecting the crude extract to chromatography using a second organic solvent to obtain said sesquiterpene lactones.

7. The method of claim 5, wherein said effective amount is administered daily for at least 6 weeks.

* * * * *